United States Patent [19]

Hoshino et al.

[11] Patent Number: 5,049,750
[45] Date of Patent: Sep. 17, 1991

[54] APPARATUS AND SYSTEM FOR INSPECTING WALL THICKNESS OF SYNTHETIC RESIN CONTAINERS

[75] Inventors: Masaru Hoshino, Tokyo; Hiroaki Nose, Saitama, both of Japan

[73] Assignee: Dai Nippon Insatsu Kabushiki Kaisha, Tokyo, Japan

[21] Appl. No.: 397,443

[22] PCT Filed: Dec. 16, 1988

[86] PCT No.: PCT/JP88/01279

§ 371 Date: Aug. 15, 1989

§ 102(e) Date: Aug. 15, 1989

[87] PCT Pub. No.: WO89/05957

PCT Pub. Date: Jun. 29, 1989

[30] Foreign Application Priority Data

Dec. 16, 1987 [JP] Japan .................. 62-316081
Jan. 29, 1988 [JP] Japan .................. 63-17447
Oct. 6, 1988 [JP] Japan .................. 63-252254

[51] Int. Cl.$^5$ .................................. G01B 11/02
[52] U.S. Cl. ............................ 250/341; 250/223 B
[58] Field of Search .................. 250/223 B, 341; 209/524, 588

[56] References Cited

U.S. PATENT DOCUMENTS

| | | | |
|---|---|---|---|
| 3,150,266 | 9/1964 | Mathias | 250/223 B |
| 3,601,616 | 8/1971 | Katsumata et al. | 250/223 B |
| 4,055,252 | 10/1977 | Klamm et al. | 209/524 |
| 4,304,995 | 12/1981 | Huttunen et al. | 250/223 B |
| 4,510,389 | 4/1985 | Fumoto | 250/339 |
| 4,736,851 | 4/1988 | Ricros et al. | 209/524 |
| 4,852,412 | 8/1989 | Bogatzki et al. | 250/223 B |

FOREIGN PATENT DOCUMENTS 115571 11/1974 Japan .
169710 9/1985 Japan .

Primary Examiner—Carolyn E. Fields
Assistant Examiner—Drew A. Dunn
Attorney, Agent, or Firm—Wegner, Cantor, Mueller & Player

[57] ABSTRACT

This invention relates to an inspection system for a container made of synthetic resin, comprising: a wall thickness inspecting apparatus having a projector for emitting an inspection light guided from a light source inserted into a container made of synthetic resin and provided with one end opened towards the wall of the container, a light receiver arranged in opposition to the projector at an external portion of the container for receiving the inspection light passing through the wall of the container and converting the received light into an electric signal, and an arithmetic operation device for calculating the wall thickness of the container on the basis of the output signal from the light receiver; a first container conveying station provided with a plurality of container holders arranged around the circumference of a rotary disc with predetermined spaces; a container feeding station for feeding the containers to a container conveying passage of the first container conveying station with the interval equal to that between the adjacent holders; a first inspecting station for inspecting the existence of the heat resistant resin of the container; a second inspecting station for inspecting the wall thickness of the container; a second container conveying station provided with a container receiving end portion for receiving the container determined to be a good product by the inspections of the first and second inspecting stations and conveying the container externally of the first container conveying station.

5 Claims, 16 Drawing Sheets

APPARATUS AND SYSTEM FOR INSPECTING WALL THICKNESS OF SYNTHETIC RESIN CONTAINERS

TECHNICAL FIELD

This invention relates to an apparatus and system for inspecting a wall thickness of a container of a cylindrical bottomed structure made of synthetic resin and adapted to be filled with any kind of drink such as soft drink, juice or like drink (called merely drink hereinafter).

PRIOR ART

Recently, soft drinks have been sold in a state of being filled in a container having a large volume and, generally, the container of this type is made of a polyethylene terephthalate resin (PET resin). The drink is heated to a relatively high temperature of about 85° when the drink is filled into the container, so that an opening portion and a shell portion of the container may be deformed by the heated drink upon the filling thereof. Moreover, when the container filled with the heated drink is closed with a lid and, thereafter, cooled, an inner pressure in the container is lowered, so that the shell of the container may be deformed inwardly. Such adverse phenomenon will be caused when a container having a shell with a long longitudinal length is utilized. In order to obviate this adverse phenomenon, there has been proposed a container having the shell provided with a column like portion extending in the axial direction of the container and having a corrugated section to strengthen the structure of the shell of the container. However, the provision of such container does not necessarily adequately obviate the defects described above.

In another aspect, in order to obviate the defects, the opening portion of the container is crystallized to provide a heat resisting property or is formed of a heat resistant resin. However, in the latter mentioned method, there is a problem in that it becomes impossible to inspect the wall thickness of the container in a case where the PET resin and the heat resistant resin have the same color or are both transparent. In the meantime, regarding the shell of the container, a destructive inspection based on a sampling method can be utilized for the inspection of products, but this inspection involves unstable requirements for the manufacture of the container and, particularly, in a case where there is a fear of an unforeseen occurrence of a faulty product, it is absolutely necessary to carry out 100% inspection of the containers.

Taking the above matters into consideration, the applicant of this application has proposed an inspection method and device, for the opening of the container, for measuring an amount of a heat resistant resin by utilizing the nature of the PET resin which has the permeability, or allows the transmission of ultraviolet rays with specific wavelengths larger than that of the heat resistant resin (Japanese Patent Application No. 61-289864). The applicant has further proposed a container rotating mechanism for improving the inspection accuracy by holding the container securely and smoothly rotating the same (Japanese Patent Application No. 62-7743). According to the method and device proposed above, it becomes possible to incorporate a process for inspecting the heat resistance of the opening portion of the container into a continuous automatic container manufacturing line. It becomes also possible to measure, at the same time, the degree of transparency, verticality, height, amount of bubbles in the opening portion and air tightness of the container.

With the inspection to the heat resistance of the container, the inspection of the opening portion can be sufficiently made by measuring the amount of the heat resistant resin of the opening, whereas it is absolutely necessary for the inspection of the shell portion to measure the wall thickness of the shell because it is required for the container to have some degree of thickness to keep the good heat resisting property of the shell of the container.

The measurement of the wall thickness of the container is performed by direct destructive means in which the shell of the container is cut and the thickness thereof is measured, or by non-contact or non-destructive means in which many kinds of rays or beams or ultrasonic waves are utilized. However, the containers have been manufactured in accordance with an automatic continuous manufacturing line, so that the utilization of a noncontact or non-destructive method is desirable for the inspection method.

DISCLOSURE OF THE INVENTION

A primary object of this invention is to provide an apparatus for inspecting a wall thickness of a container made of synthetic resin, and which is capable of inspecting with good precision the thickness by a noncontact method or a non-destructive method.

A secondary object of this invention is to provide an inspection system capable of effectively carrying out the inspection regarding the heat resistance of the container in an automatic continuous manufacturing line for containers made of synthetic resin and capable of improving the manufacturing efficiency of the containers and maintaining the stable quality of the containers.

(1) The first characteristic feature of this invention resides in the provision of an apparatus for inspecting a wall thickness of a container made of synthetic resin, the apparatus comprising a projector for projecting an inspection light, towards a wall surface of a container made of synthetic resin, emitted from a light source inserted into the container through an opening formed at one end thereof, a light receiver arranged externally on the container at a portion opposed to the projector and adapted to receive the inspection light passing through the container wall and convert the thus received light into an electric signal, and an arithmetic operating means for calculating the wall thickness of the container from the output signal from the light receiver.

(2) The second characteristic feature of this invention resides in the provision of an inspection system for a container made of synthetic resin, the inspection system comprising, in the described order, the first container conveying station in which a plurality of container holders are arranged at predetermined distances around the circumferential direction of a rotary disc, a container feeding station disposed above a circular container conveying passage of the first container conveying station and adapted to feed the containers to the first container conveying station at intervals equal to the distance between the respectively adjacent container holders, the first inspection station for inspecting the existence of a heat resistant resin at the opening portion of the container, the second inspection station for inspecting a wall thickness of the container, the second container conveying station provided with a container receiving portion for conveying the containers which are inspected and judged as products with no faults at the first and second inspection stations, and the first container discharging station for discharging the containers judged to have a fault at at least one of the first and second inspection stations.

BEST MODES FOR EMBODYING THE INVENTION

1 First Embodiment of Wall Thickness Inspection Apparatus for a Synthetic Resin Container

1—1 Basic Structure

General Structure

Figure 1:
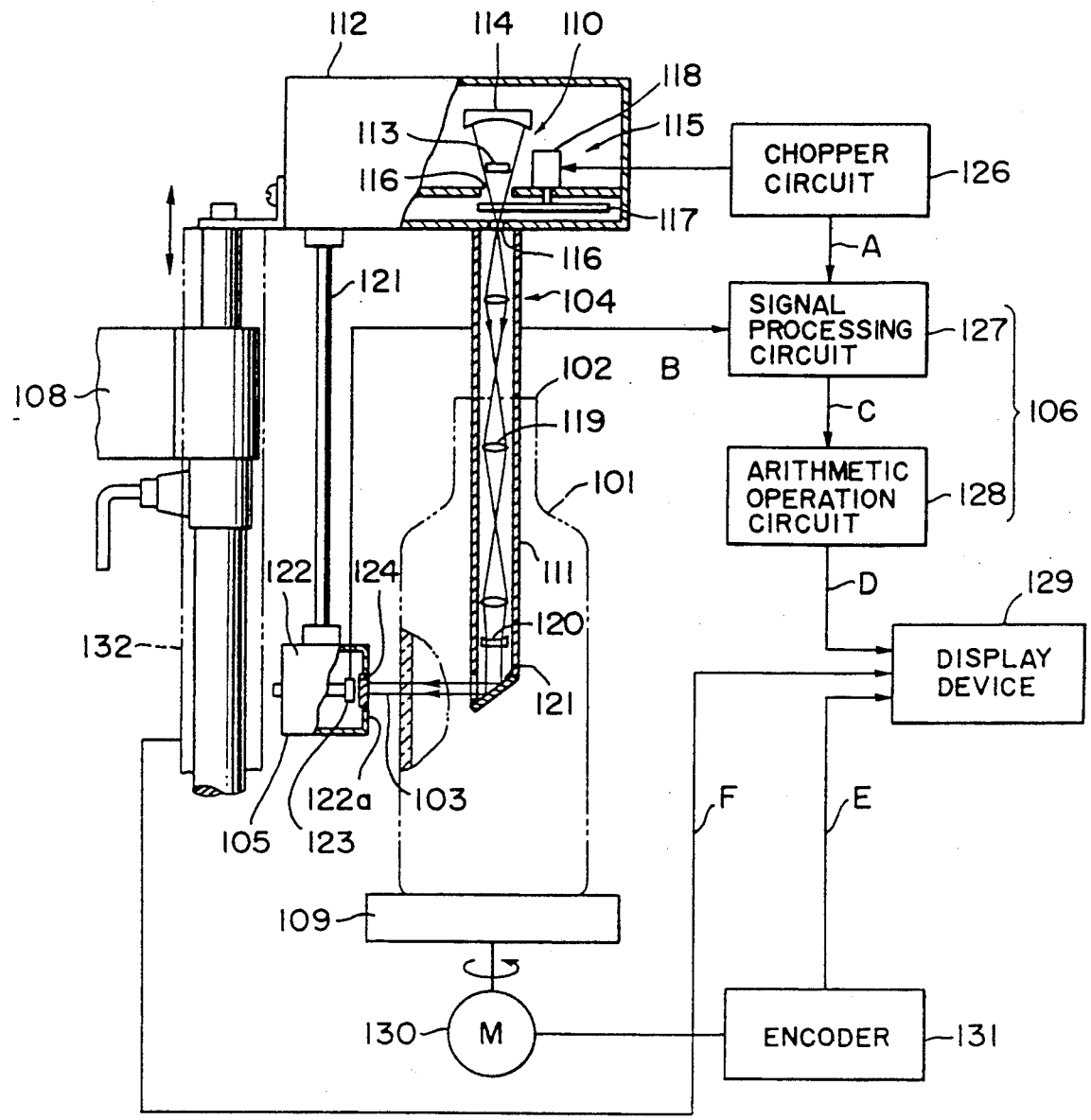
FIG. 1 is a general view of the first embodiment of an apparatus, according to this invention, for inspecting a wall thickness of a container made of synthetic resin.

FIG. 1 shows the general structure of the first embodiment of an apparatus, according to this invention, for inspecting a wall thickness of a container made of synthetic resin. Referring to FIG. 1, the thickness inspection apparatus comprises a light projector 104 inserted into a container 101, for example, preferably a bottle, through an opening 102 thereof and adapted to emit an inspection light 103 towards a shell wall of the container 101, a light receiver 105 arranged externally of the container 101 so as to oppose a light projecting portion of the projector 104 with the shell wall portion interposed therebetween with a predetermined space, an arithmetic operation unit 106 for calculating the wall thickness of the inspected portion of the container 101 in response to an output signal from the light receiver 105, an elevating means 108 for elevating the projector 104 and the receiver 105 together, and a rotating means 109 for rotating the container 101 in the circumferential direction of the container 101 at an inspecting portion. According to the construction of the inspection apparatus described, the elevating means 108 and the rotating means 109 constitutes an inspecting position changing unit, in which the rotating means is a circumferential inspecting position changing means for the container 101.

Container 101

The container, an object to be inspected, 101 is made of a synthetic resin material prepared by mixing a resin having a heat resisting property such as polyallylate resin with a PET resin. The container is thus transparent or translucent. The container 101 is formed by an injection molding method in which both the resins described are simultaneously injected into a mold. As described hereinbefore, the opening portion of the container 101 is formed by concentrating the polyallylate resin to maintain the heat resisting property at that portion. The shell wall portion of the container has a laminated structure in the thickness direction formed, as a three-layered structure, by inner and outer layers of PET resin and a layer of the heat resistant resin interposed between the PET resin layers.

Projector 104

As shown in FIG. 1, the projector 104 generally comprises a light emitting portion 110 and a light guiding portion 111.

The light emitter 110 is accommodated in a casing 112 and comprises a light source 113, a concave mirror arranged above the light source 113, a chopper 115 disposed below the same, and a pin hole 116 formed in the bottom portion of the casing 112.

The light source 113 is composed of a material, such as a nichrome wire, emitting an infrared ray as an inspection light. It is preferred to utilize infrared rays having a wavelength of 2 to 5 $\mu$m for the reason that if the infrared rays have a longer wavelength, it is necessary to elongate a light passage constituted by a lens unit and this results in the elongation of the light guide 111. As this is not practical, and if the infrared ray having a long wavelength of, for example, 15 to 18 $\mu$m is utilized, and it is necessary to utilize a blackbody furnace. The usage of the blackbody furnace makes the whole apparatus expensive.

The concave mirror 114 is located so as to concentrate the infrared rays emitted from the light source 113 and has a focal point on the pin hole 116.

The chopper 115 is arranged so as to chop the light reflected by the concave mirror 114 and towards the pin hole 116 to obtain light having a discontinuous shape, i.e. alternating wave shape. The reason for carrying out the chopping operation is based on the fact that it is necessary to eliminate variable factors such as drift and offset on the basis of the characteristics of the photoelectric transfer element provided for the light receiver 105 described hereinlater for the high precision inspection of the container and, hence, it is necessary to change the shape of the light once so as to have the alternating wave shape to deny the drift and offset and then to transfer into the D.C. shape. Such chopping operation may be performed by an electric means in which electric signals applied to the light source 113 are chopped, or by a mechanical means as in this embodiment in which the light emission from the light source is made constant, but the light therefrom is intermittently shut out by a chopper plate 117 which is rotated by an electric motor 118 with a predetermined speed of revolution.

The light guide 111 extends downwardly from the bottom of the casing 112 at a portion corresponding to the location of the pin hole 116. The inspection light 103 reflected by the concave mirror 114 and converted into the alternating wave shape by the chopper 115 is guided into the light guide 111 through the pin hole 116. A lens system 119 consisting of a plurality of lens units arranged in multistage series is arranged in the light guide 111. The inspection light 103 through the pin hole 116 is made into parallel light beams through the final stage lens unit 120 and the parallel light beams are then reflected by a reflecting mirror 121 arranged at the front end portion of the light guide 111 with an inclination of 45° with respect to the projected light. The reflected light projects as a spot light 103 towards the shell wall of the container in the form of a bottle 101.

Light Receiver 105

Figure 2:
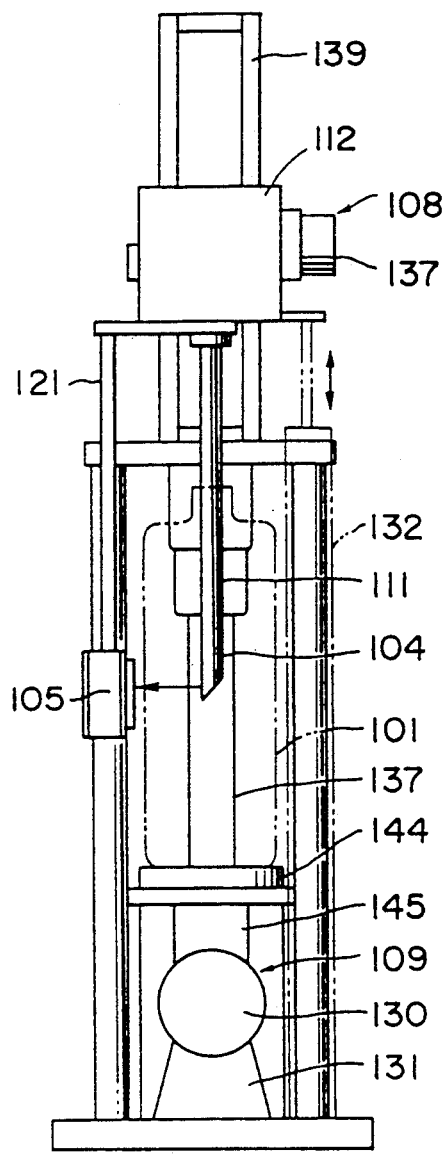
FIG. 2 is a front view showing a mechanical structure of the apparatus shown in FIG. 1.
Figure 3:
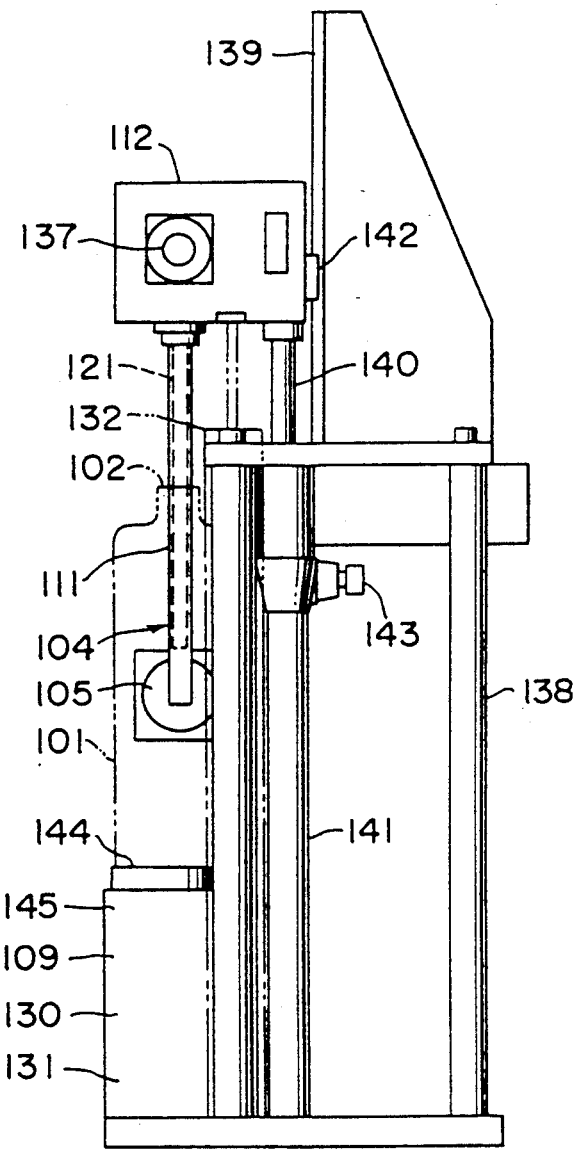
FIG. 3 is a side view showing a mechanical structure of the apparatus shown in FIG. 1.

As shown in FIGS. 1, 2 and 3, the light receiver 105 is attached to the casing 112 by a supporting member at a position opposing the light projecting end portion of the light guide 111, i.e. the reflecting mirror 121 with a predetermined interval in the light reflecting direction. The light projector 104 and the light receiver 105 are always integrally held with a constant relative relationship maintained therebetween.

The light receiver 105 comprises a casing 122 provided with a light receiving window 122a, an interference filter 124 provided for the window 122a and a photoelectric transfer element 123 disposed behind the interference filter 124. The interference filter 124 has the charactthe characteristics to filter the specific wavelength (2.6 μm) as a peak so as to accord with the spectral characteristics relative to the thickness of the container 101 and to shut out unnecessary wavelengths of the external disturbance noise. The photoelectric transfer element 123 is usable at a usual temperature or a constant temperature and it is desired that the spectral characteristics are made to peak at the wavelength of 2 to 5 μm in accordance with the inspection light 103 for improving the SN (signal-to-noise) ratio. A PbS (lead sulfide) photoelectric transfer element may be utilized for this purpose.

Electric Signal Processing Unit

The electric signal processing unit utilized for the apparatus according to this embodiment comprises, as shown in FIG. 1, a chopper circuit 126 for driving the chopper 115, a signal processing circuit 127 for converting the output signal from the photoelectric transfer element into a D.C. wave shape (peak hold wave shape) with a chopper output signal A as a timing signal, an arithmetic operating circuit 128 for calculating a wall thickness of a container shell portion to be inspected on the basis of the output signal processed by the processing circuit 127, a rotary encoder 131 for detecting the rotating position of the rotating means 109, described hereinafter, i.e. a circumferential position of the container 101, a potentiometer 132 for detecting the positions of the projecting portion of the projector 104 and the light receiving portion 105 in the axial direction of the container 101, and a display unit 129 for displaying the thickness distribution of the container 101 in the circumferential direction thereof on the basis of the operated output signal (wall thickness t) and the output signal from the encoder 131 and displaying the thickness distribution of the container 101 in the axial direction thereof on the basis of the operated output signal (wall thickness t) and the output signal from the potentiometer 132.

The chopper circuit 126 serves to output the inspection light of the alternating shape form by rotating the D.C. motor 118 at the predetermined speed of revolution and then rotating the chopper plate 117 provided with cutouts, not shown, formed intermittently along the circumferential direction thereof. The chopper circuit 126 transmits the timing signal A corresponding to the chopping period of the inspection light 103 (FIG. 6(a)). The timing signal A is then input into the signal processing circuit 127.

Figure 5:
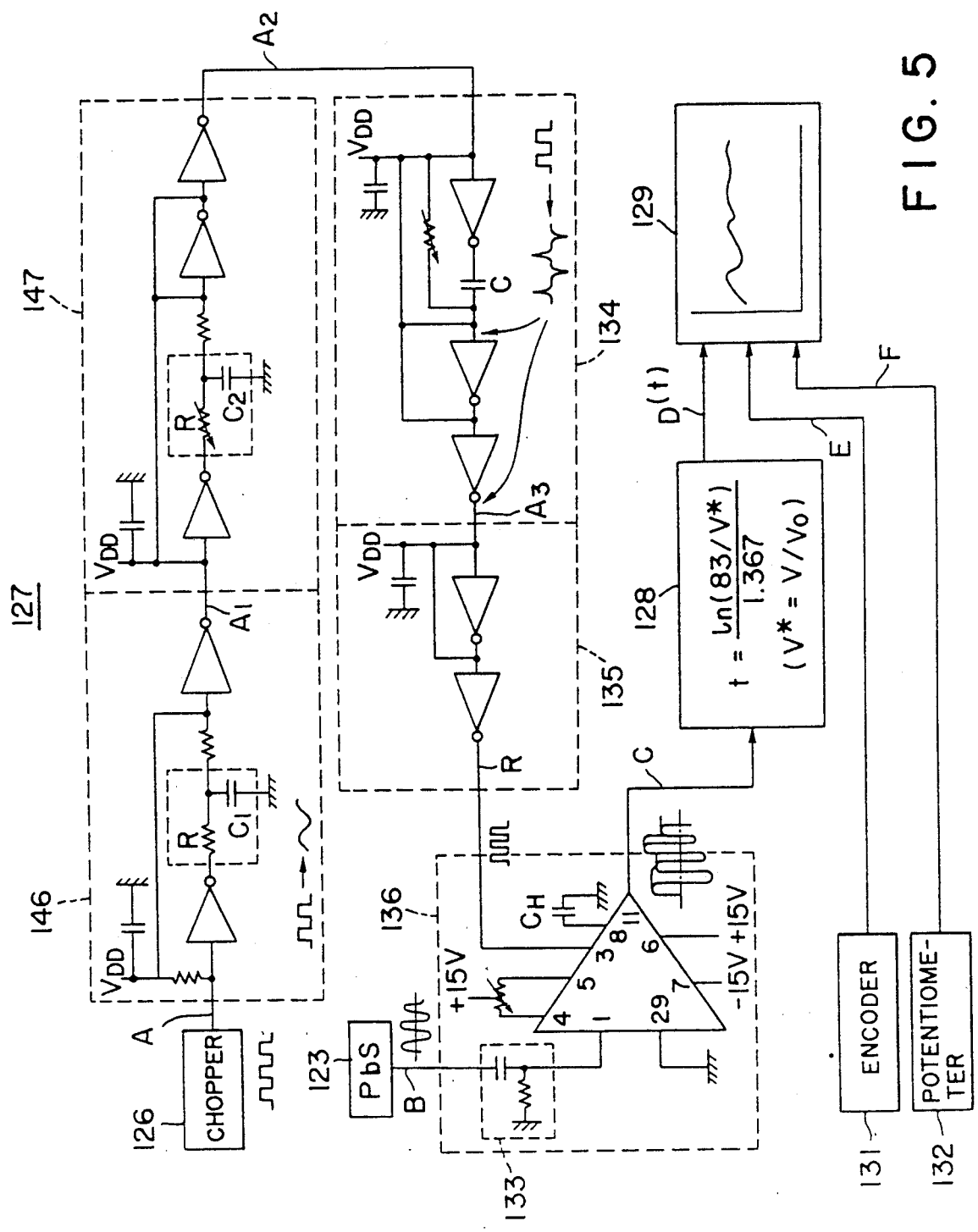
FIG. 5 is a circuit diagram for the inspection apparatus shown in FIG. 1.

The signal processing circuit 127 comprises, as shown in FIG. 5, a primary delay circuit (integrating circuit) 146 for outputting a timing signal $A_1$ generated by delaying the timing signal A by the predetermined time constant, a secondary delay circuit (integrating circuit) 147 for outputting a timing signal $A_2$ generated by further delaying the timing signal $A_1$, an edge detecting circuit (differentiating circuit) 134 for detecting the transition edge of the thus twice delayed timing signal $A_2$, a duration circuit 135 for converting the edge signal transmitted from the edge detecting circuit 134 into a signal voltage of TTL level, and a peak hold circuit 136 for peak holding the output signal from the photoelectric transfer element 123 with the converted signal being as a reset input signal R. It is to be noted that the delay circuit means is not necessarily constituted by the two staged delay circuits as described above and only one delay circuit may be utilized in a case where the single staged delay circuit ensures the delay time constant required.

Figure 6:
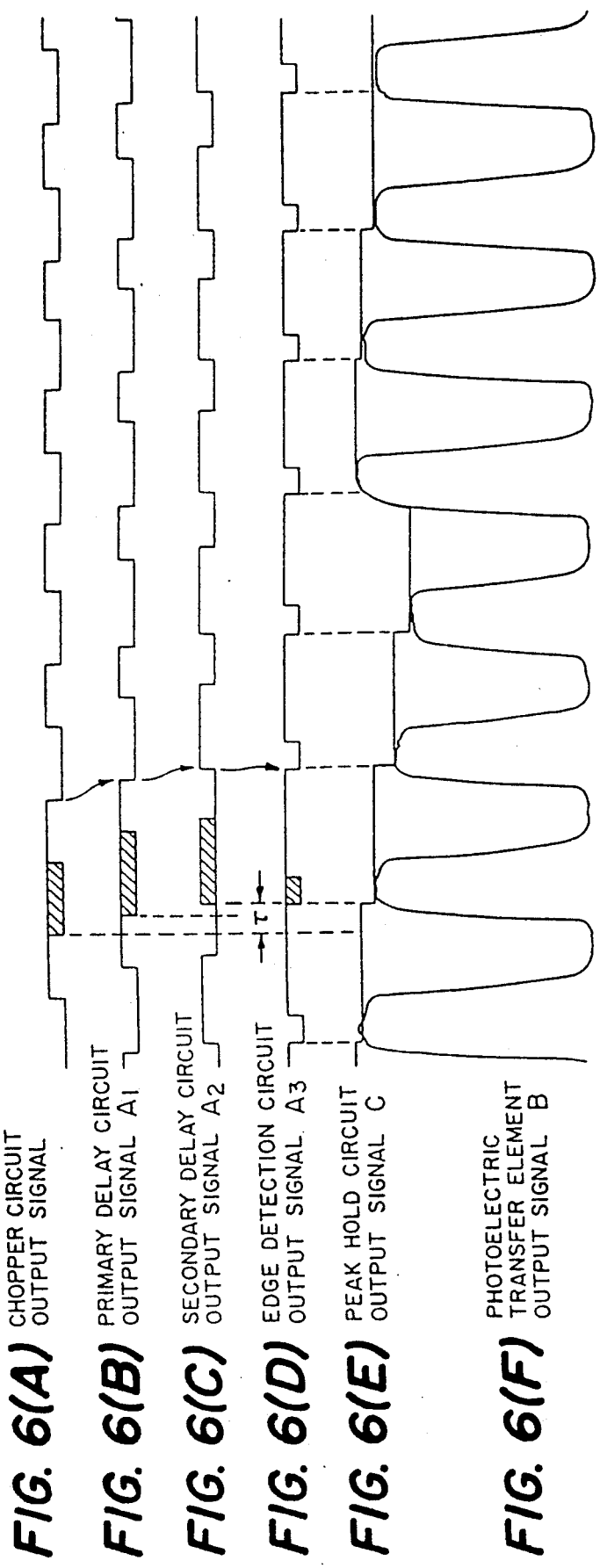
FIG. 6a, 6b, 6c, 6d, 6e, and 6f show time charts of output signals to be transmitted from the respective portions of the inspection apparatus shown in FIG. 1.

The primary and secondary delay circuits 146 and 147 are active circuits utilizing CR integrating circuits and operation amplifiers and serve to delay the output signals A from the chopper circuit into the output signals $A_1$ and $A_2$ having phases represented by FIGS. 6(b) and 6(c). The time constant $\tau$ is adjustable by rendering variable the resistance R in the CR integrating circuit.

The edge detecting circuit 134 is a differentiating circuit including a capacitor $C_O$ and serves to detect the transition edge of the timing signal $A_2$ and then to transmit an output signal $A_3$ from the edge detecting circuit 134 having an actual output of differential wave shape (FIG. 6(d)).

The duration circuit 135 serves to output the reset signal R at the TTL level (logical signal level: 5V) to be in accordance with the signal level of the peak hold circuit 136 and an open collector circuit is utilized as a circuit element. The reset signal R is transmitted to the input end terminal of the peak hold circuit 136.

The peak hold circuit 136 includes a ground holding capacitor $C_H$ to hold the peak level of an output signal B to the next peak and to output a value corresponding to the wall thickness of a portion to be inspected of the container 101. This means the equivalency of the conversion into D.C. signal only in view of the peak of the alternating signal in the chopper period. Reference numeral 133 designates a bypass filter for eliminating the drift of low frequency contained in the output signal B from the photoelectric transfer element 123.

Figure 7:
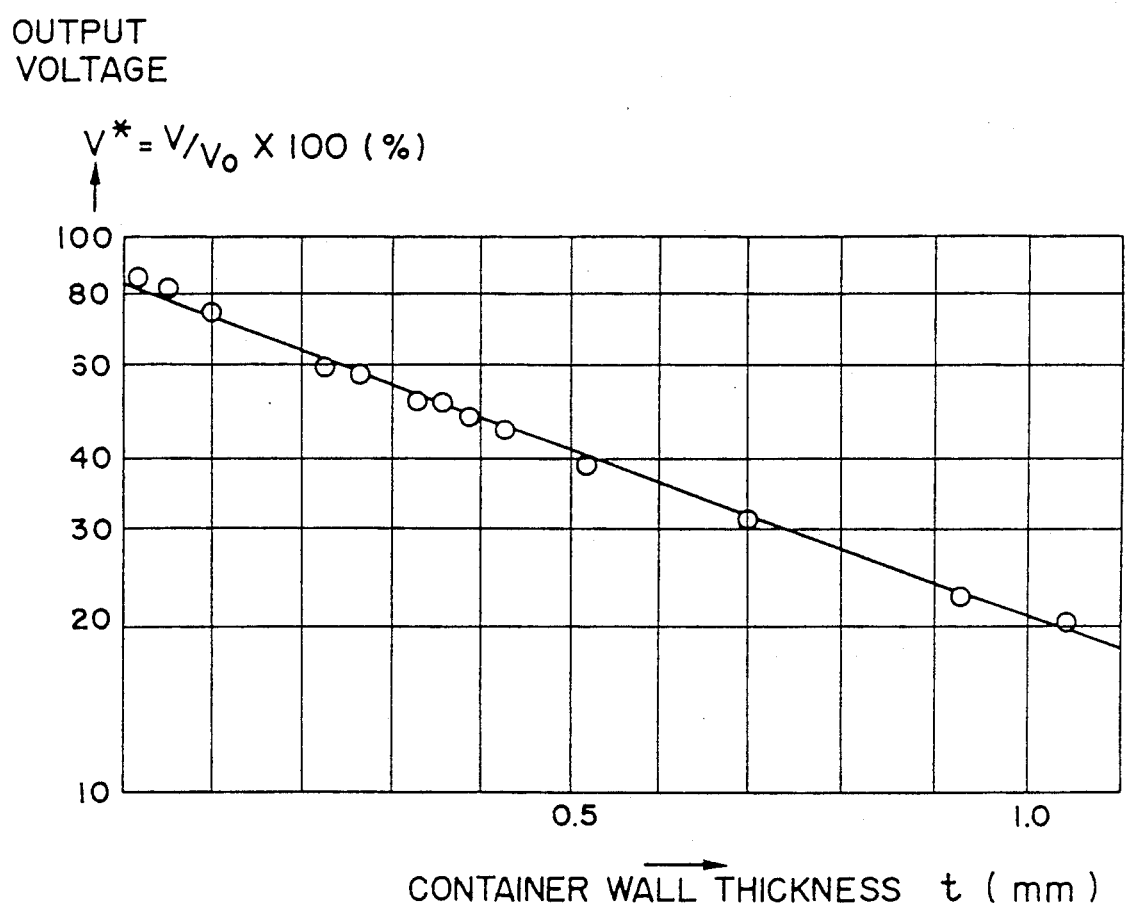
FIG. 7 shows a graph representing the relationship between the wall thickness of the container and the output voltage of a photoelectric transfer element.

The arithmetic operation circuit 128 serves to calculate the shell wall thickness t of the container 101 from the relative relationship between the output obtained from the photoelectric transfer element 123 (i.e. transmitting amount of the inspection light through the shell wall of the container 101) and the thickness t of the container 101. FIG. 7 represents a graph showing the relationship described above, in which the output voltage V is divided by the initial output voltage $V_O$ to become dimensionless in view of the initial output voltage inclusive of variable of the photoelectric transfer element 123. In the experimental example, the output voltage V* made to be dimensionless is expressed as follows.

$$V^* = 83 \times exp(-1.367t)$$

This equation is modified as follows.

$$t = ln(83/V^*)/1.367 \qquad (1)$$

where $V^* = V/V_O \times 100$; V: actual output voltage; and $V_O$: initial output voltage. Accordingly, the wall thickness t can be immediately calculated when the voltage V of the output signal B of the photoelectric transfer circuit 123 is obtained. Such arithmetic operation circuit 128 may be realized by utilizing a logarithmic amplifier set to a constant satisfying the above equation (1) or a calculating element such as a personal computer.

The display unit 129 may utilize an X-Y recorder, for example. When it is required to display the distribution of the wall thickness of the container in the circumferential direction thereof, the encoder 131 outputs a signal E regarding the circumferential directional measuring position into the X-axis input terminal and an output signal D (thickness t) from the arithmetic operation circuit 128 into the Y-axis input terminal, to thereby confirm the matching of the display to the standard specification. In case of the display of the distribution of the axial thickness of the container 101, the display may be obtained by inputting a signal F regarding the axial measurement position from the potentiometer 132 into the X-axis input terminal and inputting an output signal D from the arithmetic operation circuit 128 into the Y-axis input terminal.

Elevating Mechanism 108

The elevating mechanism 108, as shown in FIG. 2 or 3, comprises an electric motor 137 secured to the casing 112, an elevation guide 139 mounted on a supporting column 138, an elevation guide rod 140 for precisely performing the elevating motion, and a supporting member 141 for supporting the elevation guide rod 140. A rack, not shown, is disposed to a portion of the casing 112 corresponding to the location of the elevation guide 139 and a pinion, not shown, which is meshed with the rack is disposed on the side of a slider 142. According to this construction, when the pinion is rotated by the motor 137, the casing 112 is moved in the vertical direction. Reference numeral 143 designates a lock lever for locking and holding the light projecting portion of the light guide 111 of the projector 104 at an optional position. The motion of the elevation guide rod 140 is restricted by clamping the lock lever 143. Accordingly, the light guide 111 and the light receiver 105 secured to the casing 112 are both elevated together with the guide rod 140, so that the axial inspection of the container can be thus made.

Rotating Mechanism 109

The rotating mechanism 109, as shown in FIGS. 2 and 3, comprises a turntable 144 on which the container 101 can be held in a standing condition and a change gear 145 for changing the rotation speed of the turntable 144 so as to be rotated with proper revolution numbers and transmitting the changed revolution numbers. The turntable 144 is independently rotated without being synchronized with the chopper output signal A. For this reason, the encoder 131 is located for making clear the circumferential position of the container. The circumferential inspection of the container 101 can thus be made possible. The independent rotation of the turntable 144 is made in consideration of the optional change of the rotation of the container 101.

1-2 Inspecting Operation due to Basic Structure

A series of inspecting operations is performed in the following manner.

Figure 4:
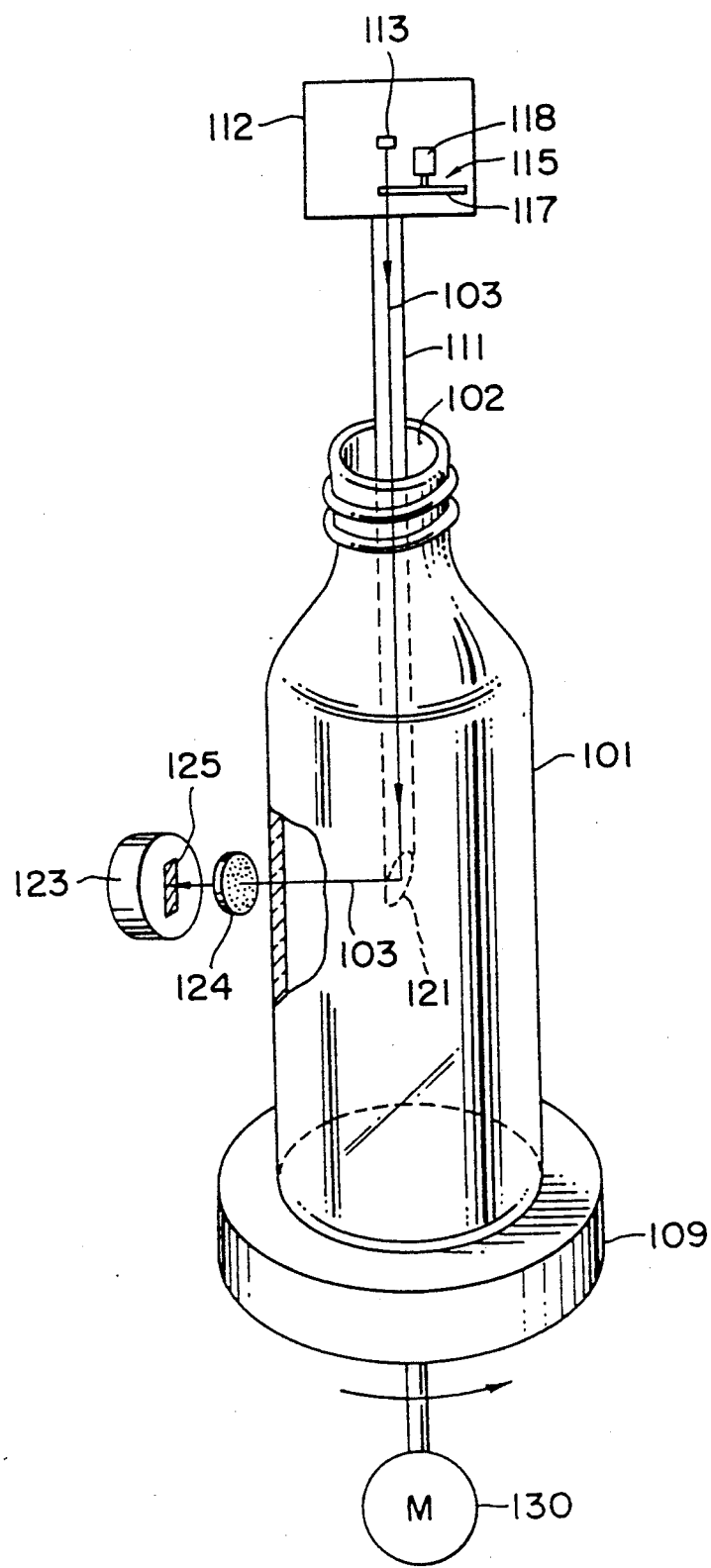
FIG. 4 is a perspective view showing the standing condition of the container and the arrangement of a projector and a light receiver in the inspection apparatus shown in FIG. 1.

A container 101 as an object to be inspected is first mounted on the turntable 144 (FIG. 4). The elevation mechanism 108 is then operated to lower the casing 112 together with the light guide 111 so as to insert the light guide 111 into the container 101 through the opening 102 thereof (FIG. 4). Upon the stoppage of the turntable 144 at a predetermined inspecting position, the inspection light 103 is emitted from the light emitting portion 110 and the inspection light 103 is chopped during this time. The inspection light 103 is guided in the light guide 111 through the lens arrangement 119, reflected by the reflecting mirror 121 and then projected outwardly from the interior of the container 101 through the shell wall thereof. The inspection light 103 through the shell wall is received by the photoelectric transfer element 123 of the light receiver 105, from which an output signal B having a magnitude corresponding to the transmitting light amount is transmitted (FIG. 5 and FIG. 6(f)). The output signal B from the photoelectric transfer element 123 is then transmitted into the signal processing circuit 127 and the chopper output signal A is also input into the signal processing circuit 127.

The signal processing circuit 127 serves to delay the phase of the chopper circuit output signal A in two stages by the delay circuits 146 and 147 (FIG. 6(c)) for the purpose of the synchronism for sampling the peak value by means of the peak hold circuit 136 (FIG. 6(e)). This delayed phase $\tau$ is detected by the edge detection circuit 134 and the reset signal R (i.e. edge detection circuit output signal $A_3$, FIG. 6(c)) is transmitted to the peak hold circuit 136. Accordingly, when the reset signal R is input, the peak hold circuit 136 serves to reset the peak value held at this time and to perform the sampling of a new peak value FIG. 6(e). A value C in this sampling corresponds to the wall thickness t of the container 101. The sampling value C is then transmitted to the arithmetic operation circuit 128, which outputs the signal D corresponding to the wall thickness t in accordance with the equation (1) described before.

During this period, the signal E representing the rotating position of the turntable 144 (i.e. circumferential position of the container 101) is input into the display unit 129, into which the signal D representing the wall thickness calculation is also input, whereby the thickness distribution in the same direction is displayed on the display unit 129.

In the meantime, when the rotation of the turntable 144 stops and the light guide 111 is elevated, the signal F representing the inspection position in the axial direction of the container is transmitted from the potentiometer 132 into the display unit 129 and the wall thickness calculation signals D corresponding to the respective inspection position signals F are recorded, whereby the thickness distribution in the axial direction can be obtained.

1-3 Effects

According to the first embodiment described hereinbefore, the following effects will be attained.

(1) A wall thickness of a container can be precisely inspected by a non-contact and non-destructive method. Accordingly, a container having a constant wall thickness can be manufactured, whereby the quality of the manufactured container can be improved.

(2) The thickness inspection can be performed with respect to every portion including the circumferential direction or the axial direction of the container such as bottle by an inspection position changing means, whereby the 100% inspection of the bottle can be performed and detailed analysis data regarding the wall thickness of the bottle can be obtained.

2 Second Embodiment of Wall Thickness Inspection Apparatus for Synthetic Resin-made Container

2-1 Basic Structure

The second embodiment of an inspection apparatus, according to this invention, for inspecting a wall thickness of a container made of synthetic resin will be described hereunder with reference to FIGS. 8 to 16.

Figure 8:
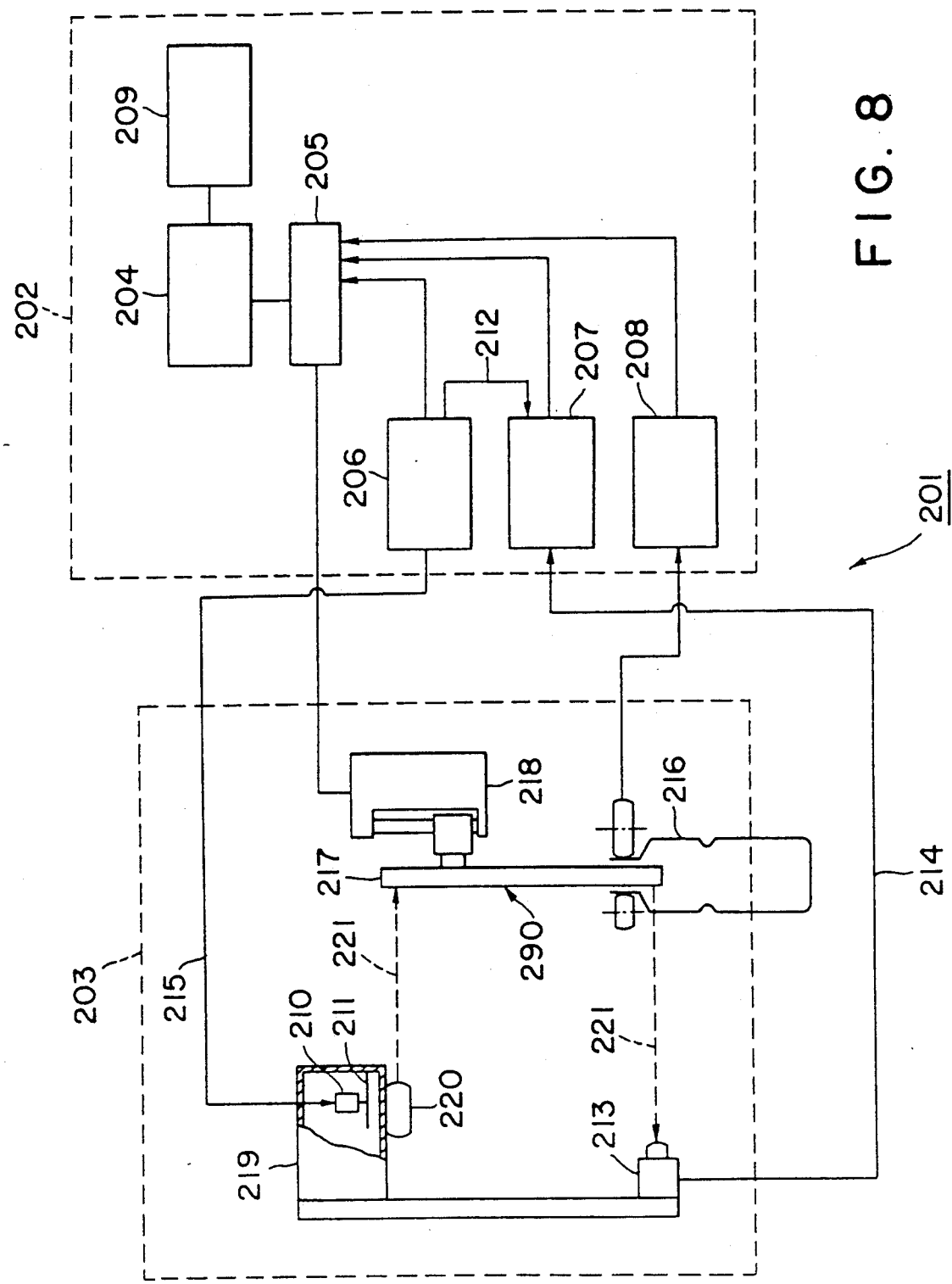
FIG. 8 is an illustration of the general arrangement of the second embodiment of an apparatus, according to this invention, for inspecting the wall thickness of a container made of synthetic resin.

The inspection apparatus 201 of the second embodiment comprises, as shown in FIG. 8, an arithmetic control operation unit 202 for performing the control of the entire apparatus and arithmetic processing of the data and an inspection unit 203 for inspecting the wall thickness of a container.

The control-operation unit 202 comprises a main controller 204 for managing the control of the whole apparatus, an interface controller (IF controller) 205 for controlling the giving and taking of the data between the inspection unit 203, etc., a chopper driver 206 for driving the chopper, a signal processor 207 for converting output signals form the chopper and the light receiver, described later, into D.C. wave shapes, a rotary encoder 208 for detecting the position of rotation of a device 250, described later, for continuously and automatically rotating and conveying the container, and an arithmetic operation processor 209 for performing the operation processing of the data.

The chopper driver 206 serves to rotate a chopper plate 211 at a constant speed at revolution under the control of the revolution number of the motor with a rotation control signal 215 and to output a timing signal 212 corresponding to the chopping period into the signal processor 207.

The signal processor 207 serves to convert an output signal 214, based on the timing signal 212, from a light receiving element 213 into a D.C. wave shape (peak hold wave shape) and to transmit the thus obtained wave shape into the main controller 204 through the IF controller 205.

The rotary encoder 208 serves to detect the position of rotation of the container rotating and conveying device 250, to convert the thus detected value into an electric signal and to output the signal into the main controller 204 through the IF controller 205.

The inspection unit 203 comprises a light projector 290 provided with an insertion tube 217 to be inserted into a container 216 made of synthetic resin, a controller 218 for controlling the elevation of the insertion tube 217 into and out of the container 216, a light emitting source 219 for emitting an inspection infrared ray 219, a light emitter 220 for emitting the inspection infrared ray to the insertion tube 217, and a light receiver 213 for converting the infrared ray from the insertion tube through the shell wall of the container 216 into an electric signal having a magnitude corresponding to the amount of the infrared ray received by the light receiver 213.

Figure 9:
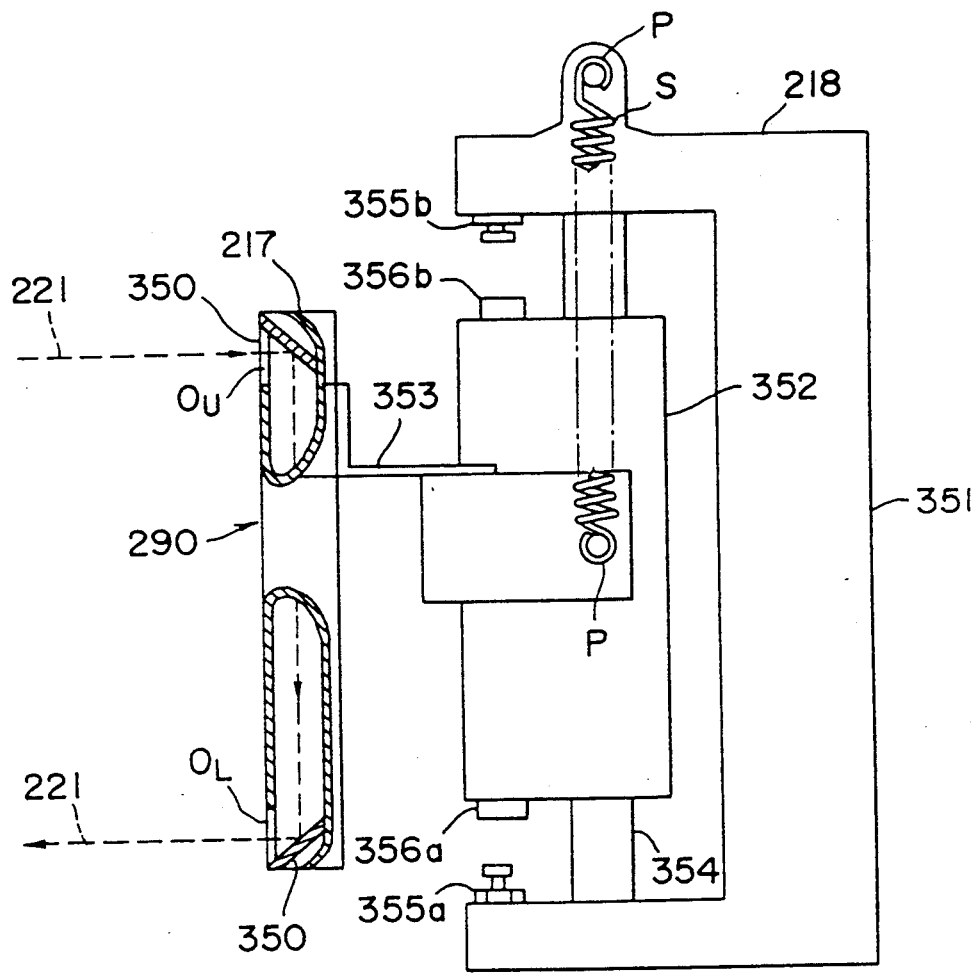
FIG. 9 is a brief side view of an insertion tube and a controller for the elevation of the insertion tube used for the apparatus shown in FIG. 8.

FIG. 9 shows a general view of the light projector 290 provided with the insertion tube 217 and the insertion tube elevation controller 218, in which the insertion tube 217 is illustrated partially in section for the purpose of explanation.

Referring to FIG. 9, the insertion tube 217 has a cylindrical configuration having upper and lower end portions and openings OU and OL are formed on the side portions of both the end portions of the insertion tube 217. Reflecting mirrors 350 are disposed inside the openings. The inspection infrared ray 221 guided into the insertion tube 217 through the opening OU, for example, is reflected by the reflecting mirrors 350 and projected towards the shell wall of the container through the opening OL as shown by a dotted line.

In a modification, a lens system may be arranged in the insertion tube 217 as occasion demands, and prisms may be substituted for the reflecting mirrors 350.

The insertion tube elevation controller 218 comprises a main frame 351, a pneumatic, i.e. air, cylinder assembly 352 for vertically moving the insertion tube 217, an insertion tube holder 352 for securing the insertion tube 217, a guide rod for guiding the pneumatic cylinder assembly 352, adjusters 355a and 355b for adjusting the vertical stop limit positions of the insertion tube 217, shock absorbers 356a and 356b for absorbing the shocks at the insertion tube movement stop time, and return spring securing pins P and P.

Figure 10:
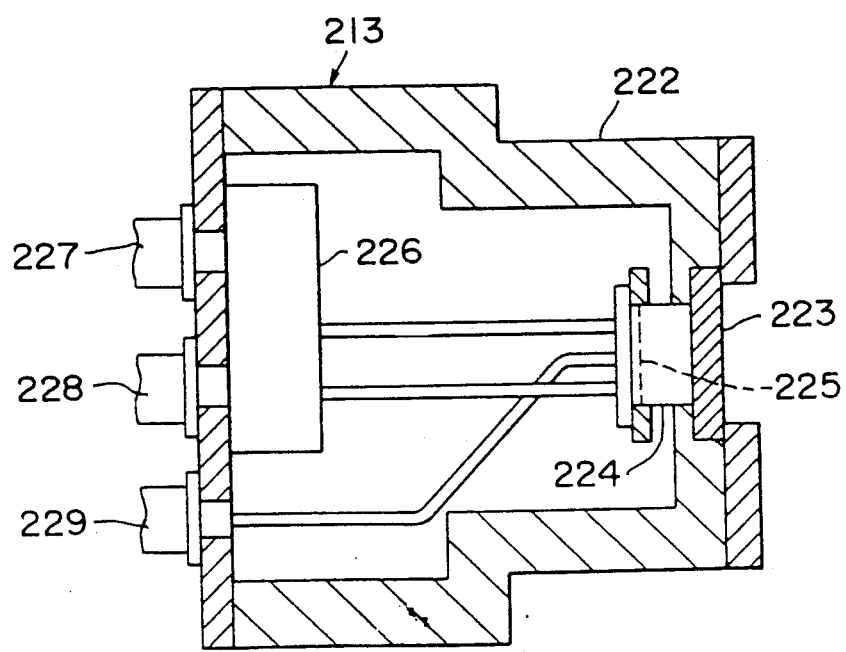
FIG. 10 is a sectional view of a light receiving sensor of the inspection apparatus shown in FIG. 8.

FIG. 10 shows a general view of the light receiver 213.

Referring to FIG. 10, the light receiver comprises an outer casing 222, an interference filter 223 for cutting out a frequency area except for the specific frequency area of an infrared ray, PbS photoelectric transfer element 224 for converting the infrared ray into an electric signal having a magnitude corresponding to the amount of the projected infrared ray, an electronic cooling element 225 accommodated in the photoelectric transfer element 224 for maintaining an inner temperature of the element 224, an amplifier 226 for amplifying the output signal from the photoelectric transfer element 224, a power source connector 227 for supplying electric power to the photoelectric transfer element 224 and the amplifier 226, an output connector 228 for transmitting an output signal 214 amplified by the amplifier 226, and a cooling controlling connector 229 for controlling the electronic cooling element 225.

The interference filter 223 is provided with a central transmission wavelength of about 2.6 μm and the infrared ray transmitting the interference filter 223 is converted into an electric signal by the photoelectric transfer element 224, then amplified by the amplifier 226 and output into the main controller 204 through the IF controller 205.

During these operations, in order to stably operate the PbS photoelectric transfer element 224, the temperature near the photoelectric transfer element 224 is maintained to a value of about 10° C. by the electronic cooling element 225 by utilizing the Peltier effect.

Figure 11:
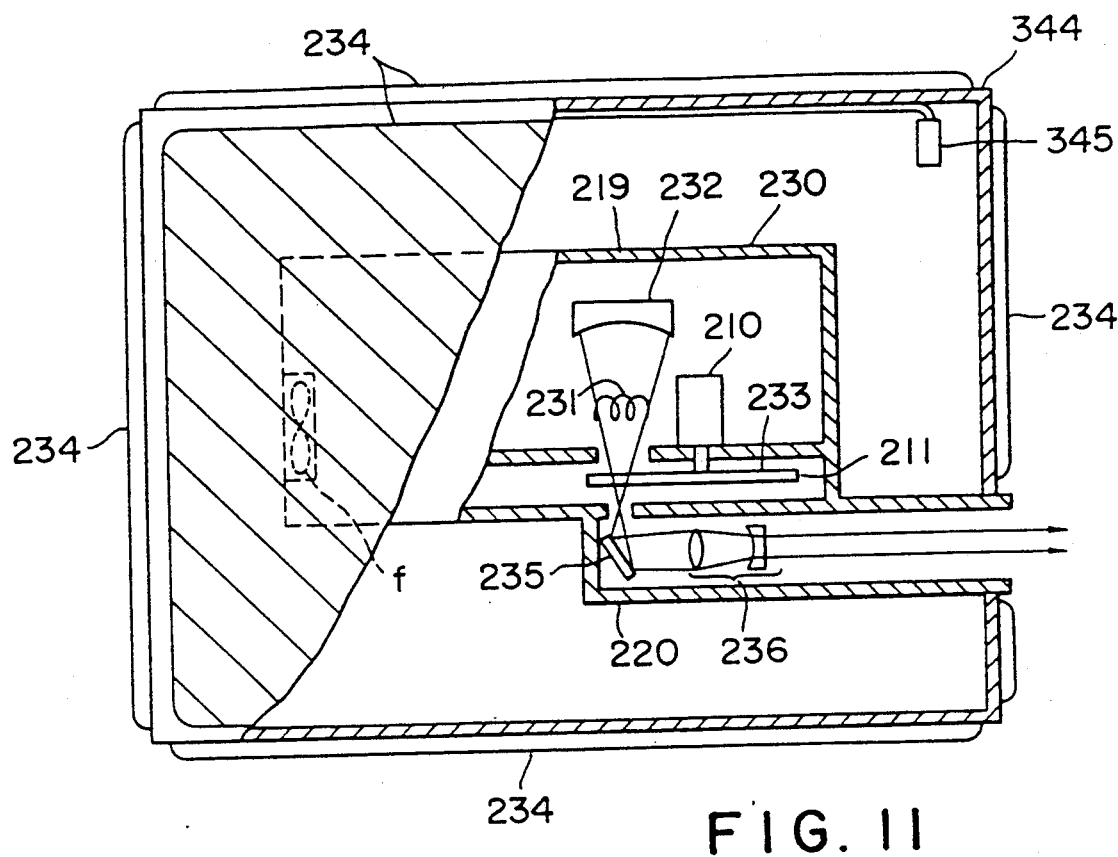
FIG. 11 is a side view partially in section of a light emitting source and a light illuminating portion of the inspection apparatus shown in FIG. 8.

FIG. 11 shows a general view of the light emitting portion 219, the light emitter 220 and a constant temperature oven 344.

Referring to FIG. 11, the light emitting portion 219 comprises an outer casing 230, a lighting source made of a filament 231, a concave mirror 232 disposed above the lighting source 231, a chopper 233 located below the lighting source 231, and a circulation fan f attached to a side plate of the casing 230. The light emitter 220 is disposed below the light emitting portion 219. As the lighting source 231 is utilized a substance such as nichrome wire for emitting infrared rays. It is desired to utilize infrared rays having a wavelength of about 2 to 5 μm.

The concave mirror 232 is located for concentrating the infrared rays from the lighting source 231.

The chopper 233 comprises a chopper plate 211 and an electric motor 210 for rotation, and serves to chop the infrared ray concentrated by the concave mirror 232 to obtain interrupted light (alternating wave shape). This chopping operation is performed for the reason such that the drift and offset caused as variable factors due to the characteristic feature of the PbS pohotoelectric transfer element are to be eliminated by converting the infrared rays into the alternating wave shape to thereby perform precise measurement. Choppers with an electrical structure in which the light source, i.e. infrared ray, is electrically chopped may be utilized as well as those of mechanical structure of the type described with reference to this embodiment.

The light emitter 220 comprises the reflector 235 and the lens system 236 and serves to introduce the infrared rays from the lighting source 231 into the insertion tube 217 as parallel beams.

Plate-like heat generating members 234 are disposed on all or some of surfaces of the constant temperature oven 344 to maintain the temperature of the interior of the oven 344 at about 40° C. The air having the constant temperature in the constant temperature oven is introduced into the casing 230 of the light source portion 219 by means of the circulation fan f to maintain the temperature constant in the casing 230 so as to stably performing the measurement by eliminating fluctuations of the lighting source 231.

Figure 12:
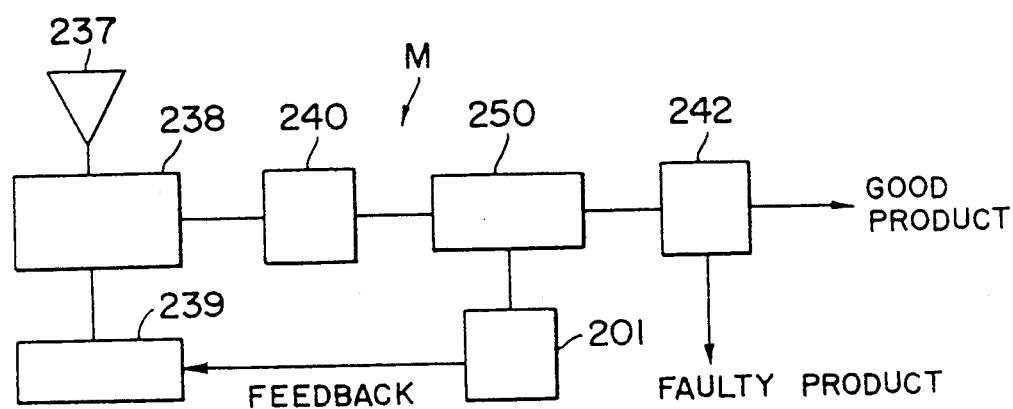
FIG. 12 is a diagram showing a synthetic resin container manufacturing system provided with the thickness inspection apparatus shown in FIG. 8.

FIG. 12 is a block diagram representing a system for manufacturing containers made of synthetic resin in which the thickness inspecting apparatus according to this invention is incorporated.

The system M for manufacturing a container made of synthetic resin comprises a material feeding device 237 for feeding a synthetic resin material, a molding unit 238 comprising an injection molding machine and a blow-forming machine, a controlling unit 239 for controlling the molding or forming condition of the molding unit 238, an inspecting device 240 for inspecting the height, for example, of a molded container 216, a thickness inspecting device 201 for inspecting the wall thickness of the container 216, a conveying and rotating device 250 for automatically and continuously conveying the container 216 to an inspecting position and rotating the same at an inspection time, and a device 242 for selecting faulty containers and good containers.

Figure 13:
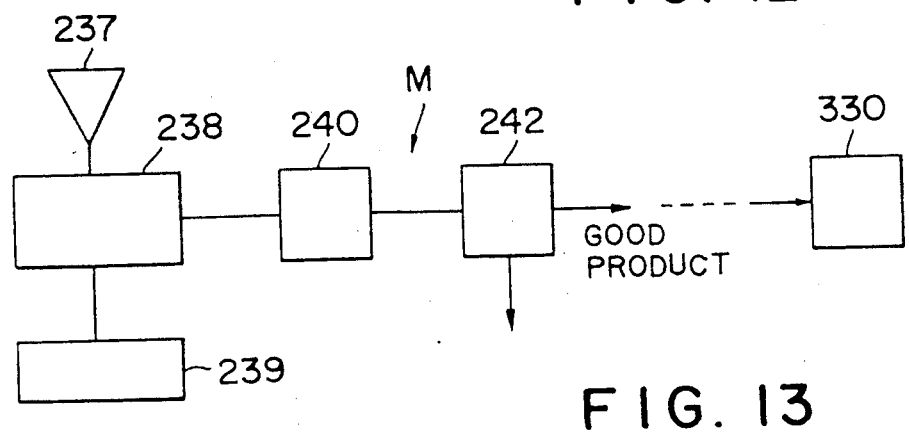
FIG. 13 is a diagram showing a synthetic resin container manufacturing system of conventional type.

FIG. 13 also shows a block diagram representing a conventional inspection system for containers made of synthetic resin and this diagram is employed for comparison with that of FIG. 12.

Referring to FIG. 13, a container manufacturing system m comprises a feeding device 237 for feeding a synthetic resin material, a molding unit 238 including an injection molding machine and a blow forming machine, a controlling unit 239 for controlling the molding and forming condition of the molding unit, an inspection device 240 for inspecting the molded container 216, and a device 242 for selecting the faulty products and the good products in accordance with the inspection. A thickness inspecting device 330 may be further provided as occasion demands, for the system for inspecting the wall thickness of the container by a manual sampling method.

The difference between the systems shown in FIG. 12 and FIG. 13 resides in that the system according to the embodiment of this invention includes the inlined type of wall thickness inspection device 201 and the container conveying and rotating device 250 arranged between the inspection device 240 and the selecting device 242. According to the provision of these further devices, the thicknesses of the containers can be continuously and automatically inspected immediately after the molding process and the data so obtained can be fed back so as to promptly implement a necessary procedure for the molding process.

Referring to FIG. 12, the material feeding device 237 feeds as a main resin material a polyethylene terephthalate type synthetic resin to the molding unit 238.

The molding unit 238 includes the injection molding machine and the blow forming machine. The injection molding machine is operated for preparing a parison for the blow formation with the resin fed from the material feeding device 237 and the parison transferred to the blow forming machine is subjected to the expansion blow formation so as to have a shape of a container. The molding conditions of the molding unit are controlled by the controlling unit 239.

The container of synthetic resin thus molded by the molding unit 238 is then conveyed to the inspection device 240.

Figure 14:
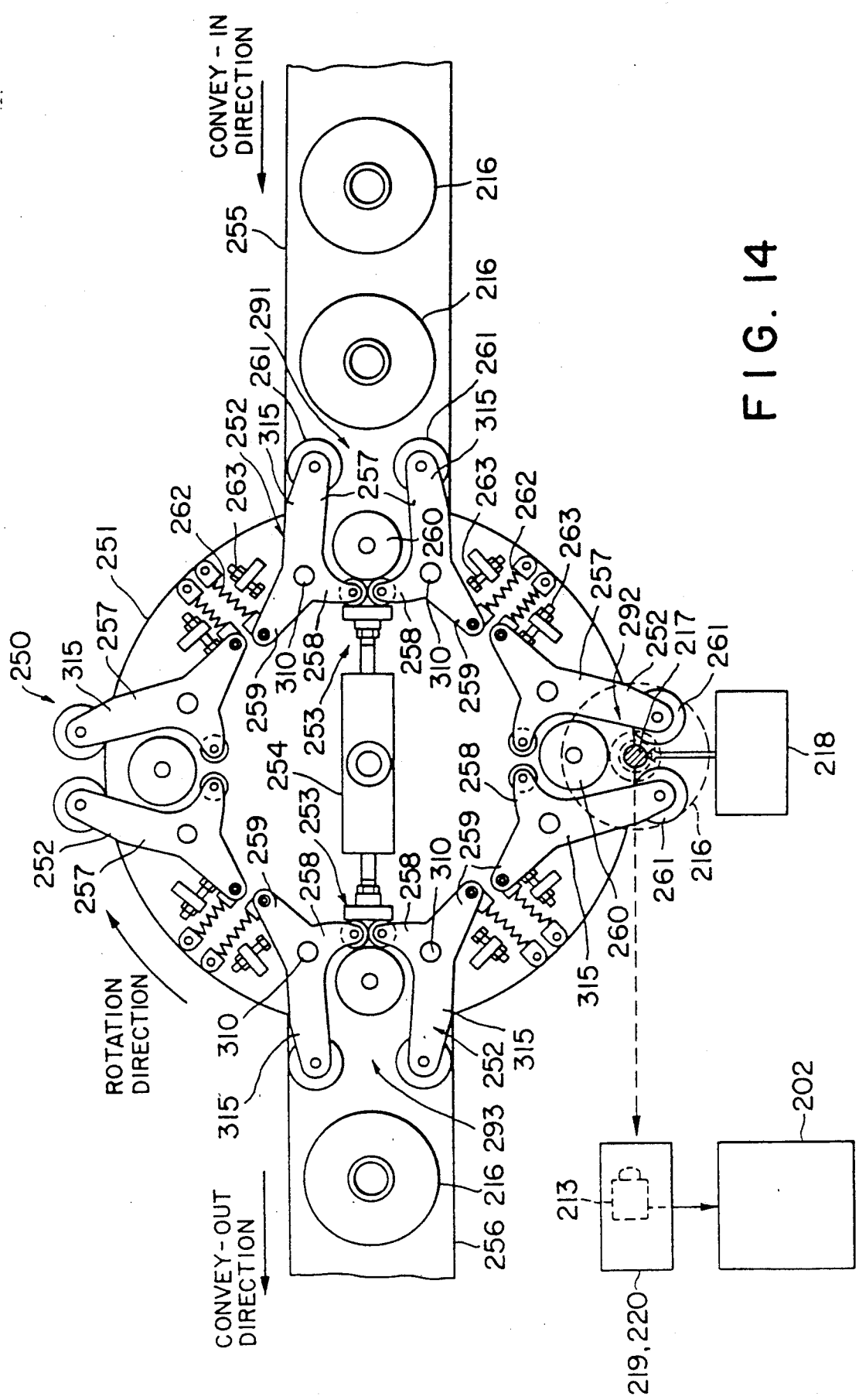
FIG. 14 is a plan view of a container rotating and conveying unit to which the inspection apparatus shown in FIG. 8 is arranged.

FIG. 14 is a detailed view of the continuously conveying and rotating device 250.

Referring to FIG. 14, the conveying and rotating device 250 comprises a turntable 251, four holders 252 mounted on the turntable 251 for holding and releasing the containers, the holders being arranged with an angular space of 90° with respect to each other, pressing members 253 for releasing the holding condition of the holders by applying pressure thereto at the container feeding and discharging times, and a cylinder assembly 254 for operating the pressing members 253.

Container take-in and take-out conveyers 255 and 256 are further connected to the turntable 251 so as to extend across the diameter of the turntable.

Each of the holder 252 includes a pair of holding members 315, each having three arm portions, for holding and releasing the container 216. The holding member 315 comprises clamp arms 257, arms 258 for opening and closing the clamp arms in association with the pressing member 253, and return arm 259 to which return springs 262 are connected to apply an urging force to close the clamp arms 257. The return arms 259 abut against return position adjusting screws 263 at the returning thereof. A roller 260 for rotating the container at the time of inspection is disposed between the paired holding members 315 and follower rollers 261 are secured to the front ends of the clamp arms 257 to rotate the container in operative association with the roller 260.

2—2 Inspection Operation of the Basic Structure

Figure 15:
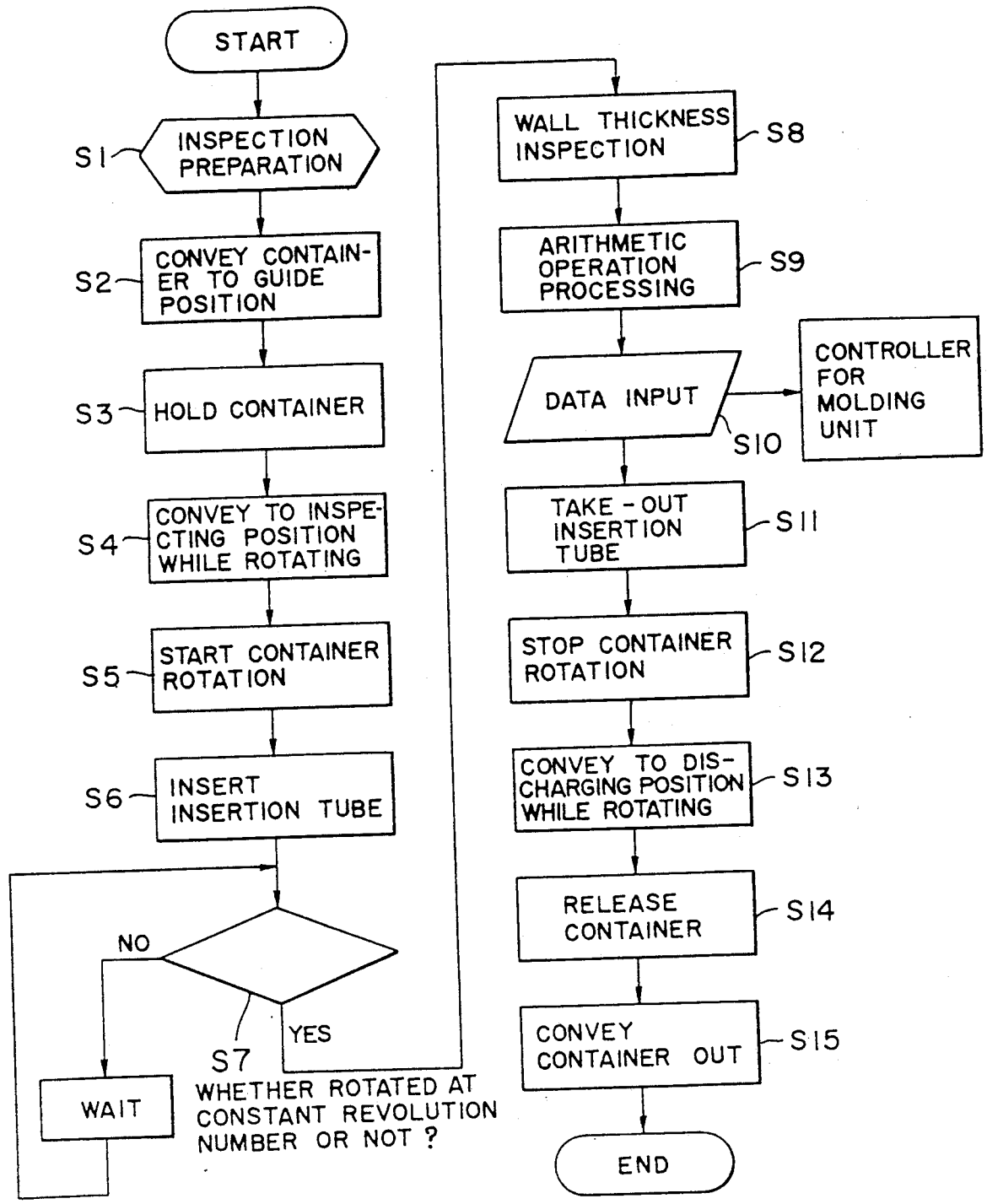
FIG. 15 is a flowchart for performing the processes of the inspection apparatus shown in FIG. 8.

The operation of the thickness inspection device will be described hereunder with reference to the flow chart shown in FIG. 15.

Preoperation for Inspection

The light source 231 and light receiving device 213 are preliminarily test operated for ensuring stable measurement.

(Step 1)

Take-in Conveying of Container

The container 216 is conveyed into an introduced position 291 by the conveyer 255 and when the introduction of the container is detected by a position detecting sensor, not shown, (Step 2), the pressing member 253 is operated by the actuation of the cylinder assembly 254 to press the arms 258 of the holding member 315 positioned at the container introduction position 291 for a thickness inspection unit operated in a continuous and automatic manner, whereby the clamp arms 257 are opened widely about pins 310 against the urging force of the return springs 262 and the return arms 259 are separated from the return position adjustment screws 263.

The container 216 is conveyed into the paired holding members 315 by the conveyer 255 with the clamp arms 257 being opened. When it is detected by a position detecting sensor, not shown, that the container 216 is conveyed to a position at which the container 216 contacts the rotation roller 260, the pressing force to the pressing member 315 is released and the return arms 259 abut against the returning position adjusting screws 263 by the urging force of the return springs 262, whereby the container 216 can be surely held by the holding members 315 by the cooperation of the roller 260 and the following rollers 261 (Step 3).

The turntable 251 is next rotated in a clockwise direction on the drawing paper and stops at a position in which the container 216 is conveyed to an inspection position 292 while maintaining the condition held by the holding members 315 (Step 4).

Thickness Inspection

The roller 260 is rotated and the container 216 and two follower rollers 261 are also rotated in association with the rotation of the roller 260 (Step 5). At the same time, the pneumatic cylinder 352 of the insertion tube elevation control unit 218 is operated to be lowered along the guide rod 354 against the urging force of the rerturn springs and the insertion tube 217 secured to the securing portion 353 also lowers into the container 216. The insertion tube 217 lowers in the container 216 by the time when the shock absorbing member (vibration preventing rubber) 356a abuts against the lowering motion stopping position adjusting member 355a. When the shock absorbing member 365a abuts against the stopping position adjusting member 355a, the pneumatic cylinder is held at that position. The vibration caused by this abuttment can be promptly absorbed by the shock absorbing member 365a to promptly keep the stable condition of the container 216 (Step 6). When the fact that the revolution number of the container 216 reaches the constant value is confirmed by the output signal from the rotary encoder 208, the main controller 204 generates instructions to commence the thickness inspection (Step 7).

The infrared rays (wavelengths of 2 to 5 $\mu$m) emitted from the light emitter 214 passes the interior of the insertion tube 217 and are projected on the container 216 through the reflecting mirror 350. The reflected light then reaches to the light receiver 213 with a part absorbed by the shell wall of the container 216 and the received light is converted into an electric signal in the light receiver 213, which is then transmitted to the signal processing unit 207. The signal processing unit 207 serves to convert the signal from the light receiver 213 into the D.C. wave shape (peak hold wave shape) on the basis of the timing signal 212 corresponding to the chopping period of the chopper driving device 206 and the converted wave shape is transmitted into the main controller 204 through the IF controller 205 (Step 8).

At the same operation time, the rotary encoder 208 detects the rotating position of the container rotating and conveying device 250 and the detected rotating position is converted into an electric signal which is then transmitted into the main controller 204 through the IF controller 205.

Arithmetic Operation Processing

The main controller 204 transfers the output signal data to the arithmetic operation unit 209 so as to convert the output signal data into data regarding the wall thickness of the container. The arithmetic operation unit 209 operates to convert the output signal data corresponding to the amount of the measured infrared ray as shown in FIG. 7 and output the thus converted data into the main controller 204 (Step 9). The main controller 204 transfers the data of the wall thickness to the controller 239 for the molding unit 238 through the IF controller 205 (Step 10)

Draw-out of the Insertion Tube

The operation of the pneumatic cylinder 352 is thereafter stopped by the instructions from the insertion tube elevation controller 218 and then elevated till the time when the shock absorbing member 356b abuts against the upper movement stopping position adjusting member 355b. The insertion tube 217 is thus easily drawn out from the container 216 (Step 11). At the same time, the rotation of the roller 260 stops and, hence, the rotation of the container 216 also stops (Step 12).

Conveying-out of the PET Container

Next, the turntable 251 is again rotated with the container 216 held and stops at the time when the holding members 315 reach the discharging position 293 (Step 13). The pressure applying cylinder assembly 254 is then operated to press the arms 258 of the holding member 315 through the pressing member 253, whereby the arms 258 are widely pivotably opened about the pins 310 against the urging force of the return springs 262 and the container 216 is thus released (Step 14). During this operation, the return arms 259 are released from the returning position adjusting screws 263.

The container 216 is then conveyed out of the clamp arms 257 by the conveyer 256 with the clamp arms 257 being opened (Step 15).

When the fact that the container 216 is discharged to the predetermined position, is detected by a position detection sensor, not shown, the operation of the cylinder assembly 254 stops to stop the pressing to the pressing member 253. Then, the pressure of the pressing member 253 is released and the return arms 259 abut against the returning position adjusting screws 263 by the urging force of the return springs 262, thus closing the clamp arms 257. The turntable 251 is again rotated and the described steps are repeated.

The container 216 is conveyed to the next station for the subsequent operations by means of the conveyer 242.

Feedback Control

The controller 239 for the molding unit 238 receiving the data regarding the wall thickness of the container performs control of the molding condition in accordance with the data.

2-3 Other Embodiments

The other embodiments will be described hereunder.

Figure 16:
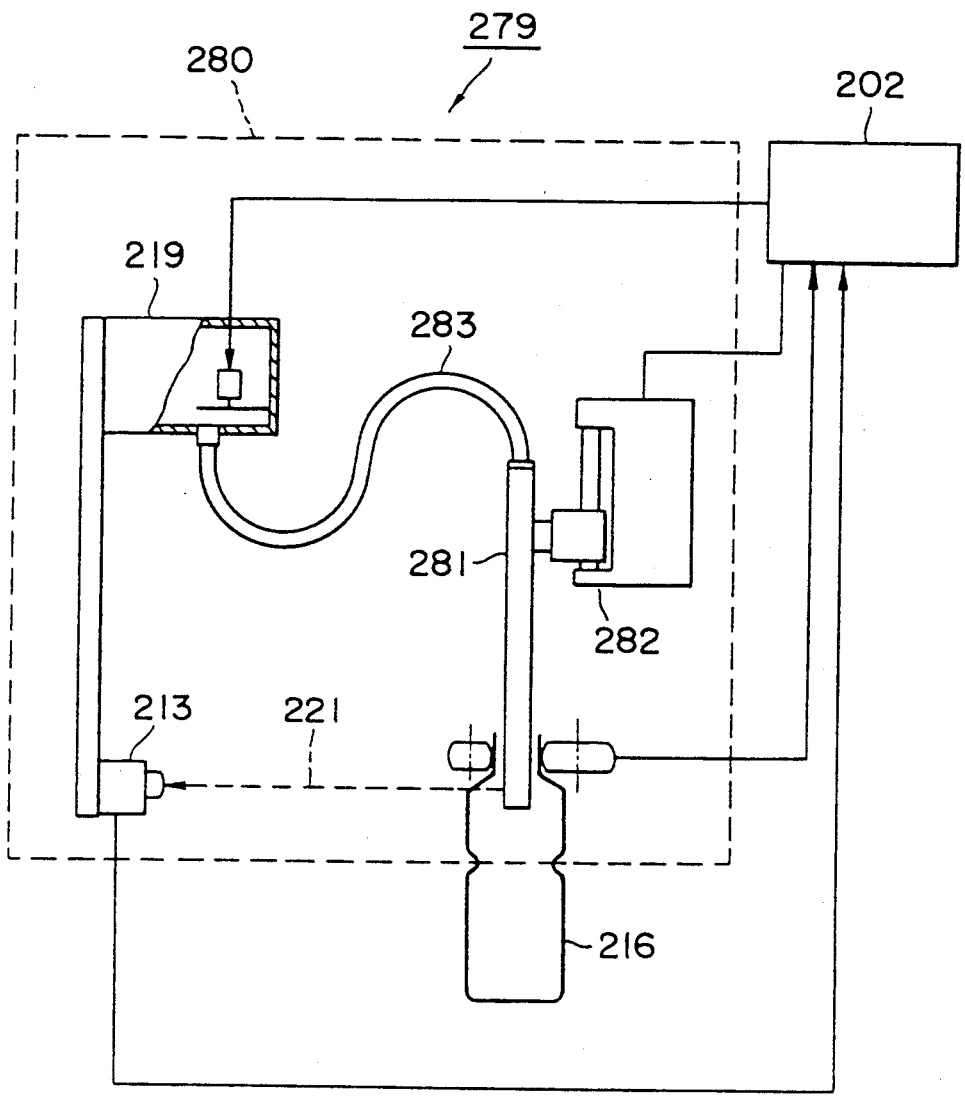
FIG. 16 shows a modification of the inspection apparatus shown in FIG. 8.

A wall thickness inspecting apparatus 279 generally comprises, as shown in FIG. 16, a control operation unit 202 for performing overall control and the operation processing and an inspection unit 280 for carrying out the thickness inspection.

The control operation unit 202 has a construction substantially the same as that of the construction described with reference to 2-1 Basic Structure.

The inspection unit 280 comprises a light source 219 for emitting an infrared ray for the measurement, a guide insertion tube 281 to be inserted into the container for introducing the infrared ray 221 for the inspection, an insertion tube elevation controller 282 for performing the insertion and the take-out of the insertion tube 281 into and out of the container 216, and a light receiver 213 for receiving the light through the shell wall of the container 216 and converting the light i.e. infrared ray into an electric signal having a magnitude corresponding to the amount of infrared rays passing through the shell wall.

The guide insertion tube 281 is formed to have a cylindrical shape into which flexible fibers 283 adapted for the infrared rays (for example, TlBrTll fluoride glass fibers) are accommodated and one end of the fiber flux is connected to the light source 219. The insertion tube 281 is inserted into the container 216 to be inspected by the insertion tube elevation controller 282 and the infrared ray 221 generated from the light source 219 for the inspection is introduced into the container 216 through the fibers 283 accommodated in the insertion tube 281.

With the embodiment shown in FIG. 16, the inspecting operation will be performed by substantially the same processes as described with reference to 2—2 Inspecting Operation.

According to this embodiment, the disturbance which may occur during the light transfer period will be reduced.

2-4 Effects

According to this embodiment, the following effects can be attained. The light projector provided with the insertion tube is constructed to be vertically movable independently, so that the construction of the entire thickness inspecting apparatus for a container made of synthetic resin can be made compact in a case where the apparatus is incorporated in the container manufacturing line and the stable measuring condition can be established in a short time.

3 Embodiment of Inspection System for Synthetic Resin-made Container

3-1 Basic Structure

An embodiment of an inspection system for a synthetic resin-made container according to this invention will be described hereunder with reference to FIGS. 17 to 20.

Figure 17:
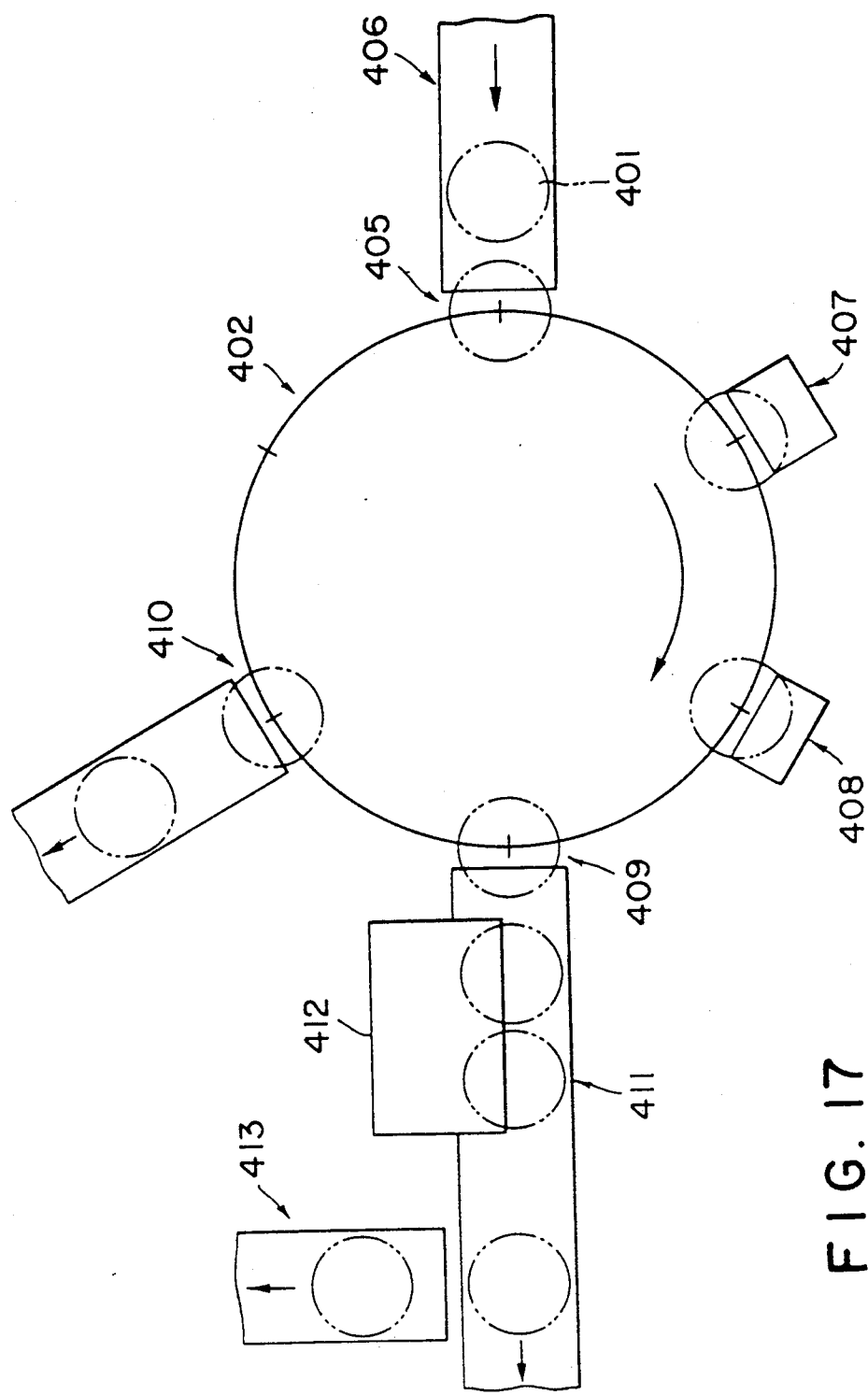
FIG. 17 is a plan view of an inspection system, according to this invention, for a container made of synthetic resin.

FIG. 17 shows a general arrangement of the inspection system for a container made of synthetic resin according to this invention and the inspection system includes the first container conveyer 402 provided with a plurality of container holders arranged around the circumference of a rotary disc 403 with equal spaces between the adjacent holders (60°, in the illustrated embodiment). Along the circular container conveying passage of the first container conveyer 402 are arranged, in the described order, a container feeding station 405 for feeding containers 401, the first inspecting station 407 for inspecting the existence of a heat resistant resin at the opening of the container 401, the second inspecting station 408 for inspecting the wall thickness of the shell of the container, a container receiving portion 409 of the second container conveyer 411 for receiving the container 401 judged to be a good product through the inspections at the first and second inspecting stations 407 and 408 and for conveying the good product externally of the system, and the first container discharging station 410 for discharging, through the second container conveyer, a container 401 judged to be a faulty product by at least one of the first and second inspecting stations 407 and 408. The second container conveyer 411 is provided with a container conveying passage along which are arranged the third inspecting station 412 for inspecting the air tightness of the container 401 and the second container discharging station 413 through which a container 401 judged to be a faulty product by the third inspecting station 412 is discharged through the second container conveyer 411.

Figure 18:
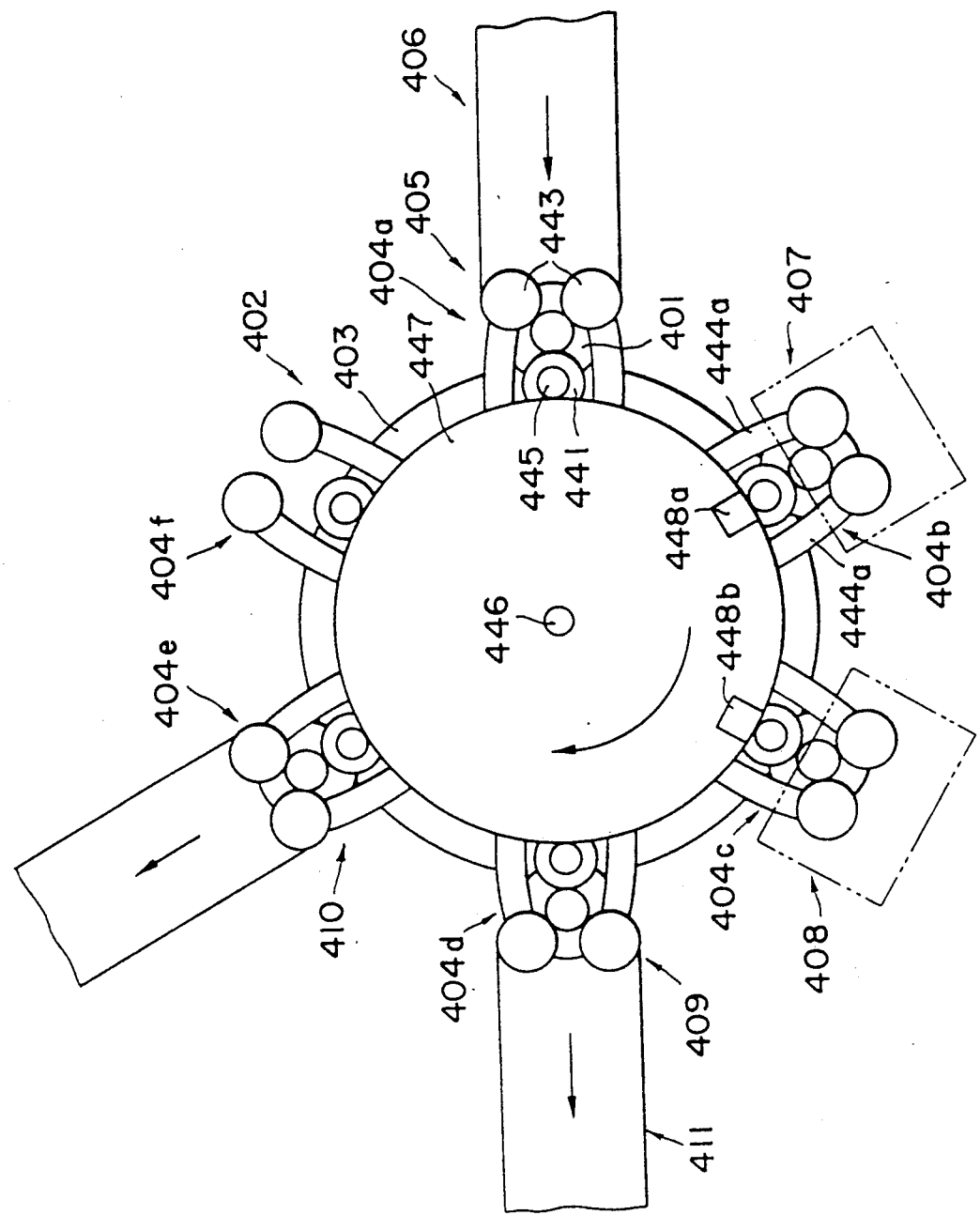
FIG. 18 is a plan view of the first container conveying station of the inspection system shown in FIG. 17.
Figure 19:
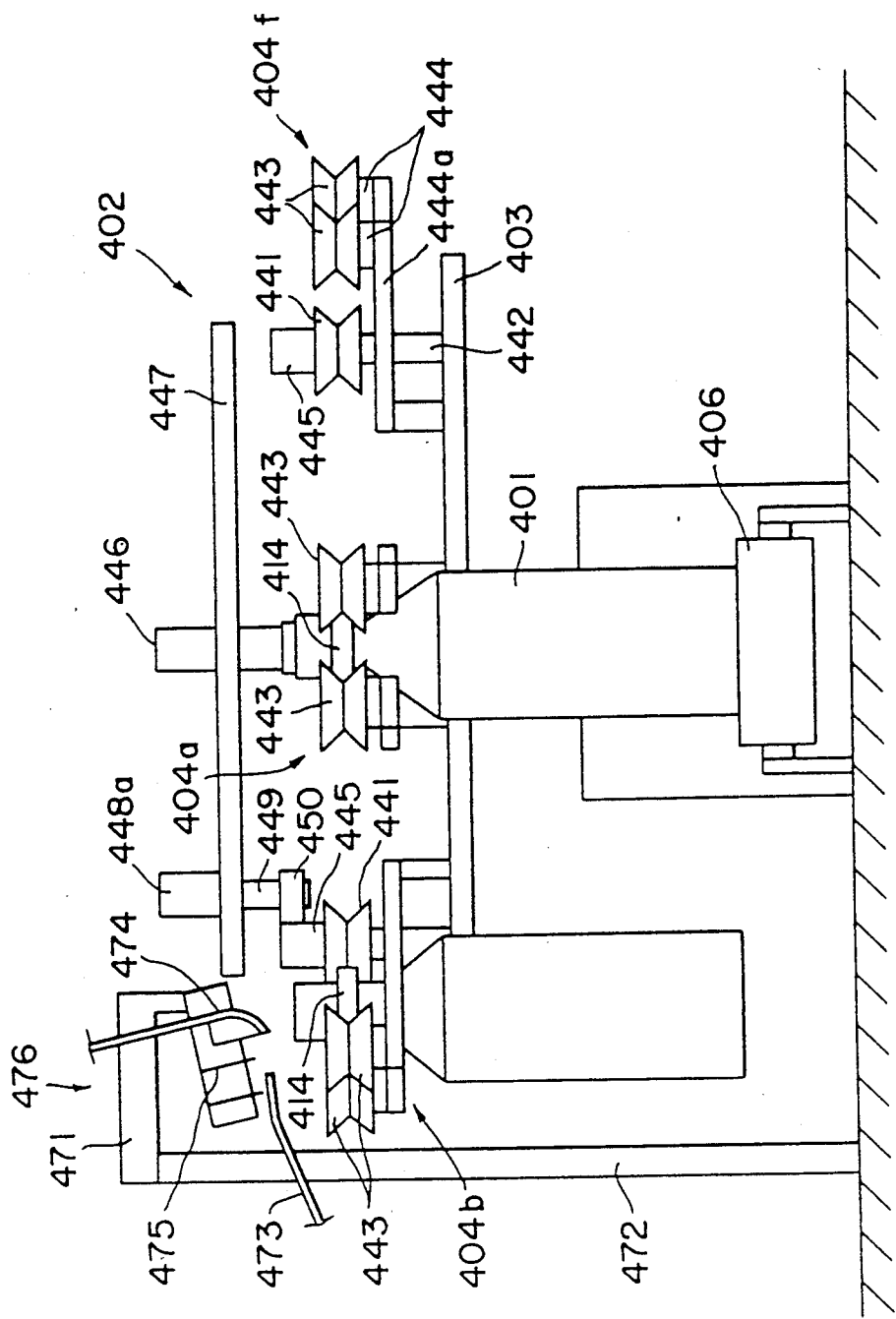
FIG. 19 is a side view of the inspection system shown in FIG. 17.

The first container conveyer 402 is provided with, as shown in FIGS. 18 and 19, a rotary disc 403 which is rotated by a driving device, not shown, together with a rotation shaft secured to the central portion of the rotary disc. The container holders 404 are arranged along the circumferential portion of the rotary disc 403 with equal spaces (six holders 404a, 404b, 404c, 404d, 404e and 404f, in the illustrated embodiment).

Each of the container holders 404 comprises a driving roller 441 mounted to a shaft 442 and a pair of rotation rollers 443 supported by a supporting rod 444 to be rotatable. Each of the supporting rods 444 is supported by an open-to-close arm 444a to be opened or closed. The respective three rollers 441, 443 and 443 are positioned at the apexes of a triangle. A rotation gear 445 is arranged on the driving roller 441 on the inner peripheral side of the rotary disc 403.

A stationary shaft 446 is mounted on the upper portion of the rotary disc 403 regardless of the rotation of the rotation shaft and a stationary disc 447 is secured to the shaft 446. Motors 448a and 448b are mounted on the peripheral portions of the stationary disc 447 with angles of 60° and 120° on the left side thereof (in the rotating direction of the rotary disc 403) with respect to the line connecting the container feeding station 405 and the shaft 446. The end of the output shaft 449 of the motor 448a (FIG. 19) is provided with a driving gear 450 which is engaged with the rotating gear 445.

The container feeding station 405 serves, as shown in FIGS. 17 and 18, to hold the container 401 conveyed by the container feeding device 406 to the first container conveyer. When the container 401 reaches the container feeding station 405, the arms 444a of the container holder 404 are opened to receive the container 401 and the flanged portion 414 of the opening of the container is nipped by the three rollers 441, 443 and 443.

The first inspecting station 407 is positioned, as shown in FIGS. 17 and 18, to a position apart from the container feeding station 405 by angles of 60° in the direction of rotation of the rotary disc 403. As shown in FIG. 19, an L-shaped sensor supporting rod 471 is located above the main structure 472 and to the front end of the supporting rod 471 is attached an inspection device 476 to which a light projecting fiber 473, a light receiving fiber 474 having a guide and a slit member 475 are secured.

The container 401 fed from the container feeding station 405 together with the rotary disc 403 by the angles of 60° in the rotating direction thereof to the first inspecting station 407 is rotated by the motor 448a through the roller 441, whereby the amount of the heat resistant resin of the opening of the container 401, the verticality, the degree of the transparency, the height, the bubble amount of the opening portion of the container 401 are inspected by the inspecting device 476 and many other inspecting devices.

The second inspecting station 408 for inspecting the wall thickness of the container 401 is positioned, as shown in FIGS. 17 and 18, to a position apart from the first inspecting station 407 by the angles of 60° in the rotating direction of the rotary disc 403.

Figure 20:
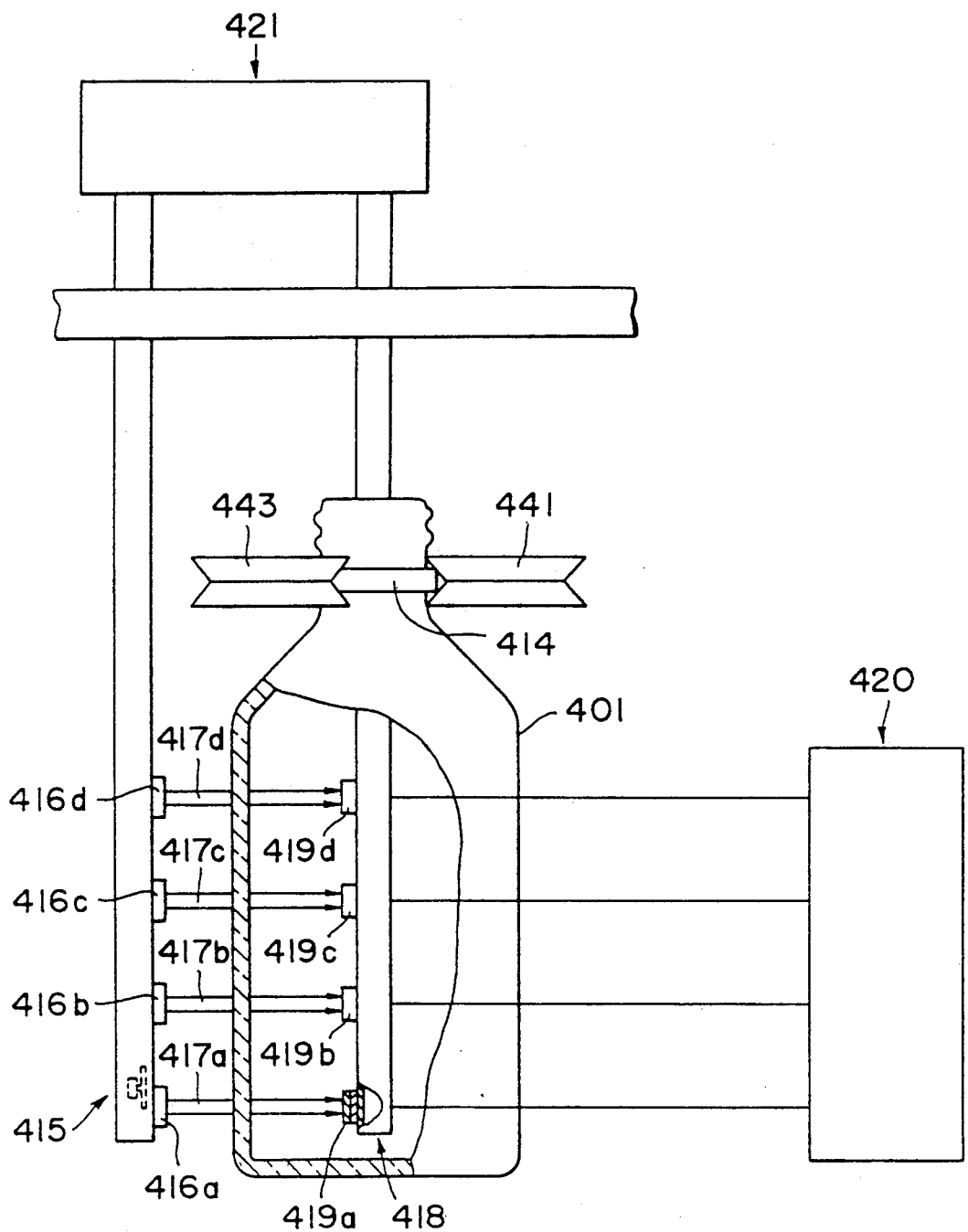
FIG. 20 is a side view, partially in section, of the second inspection station of the inspection system shown in FIG. 17.

FIG. 20 shows one example of the second inspecting station 408, which includes a plurality of light emitting elements (four light emitting elements 416a, 416b, 416c and 416d in the illustrated example) disposed externally of the container 401 and directed to the axial direction thereof. The second inspecting station 408 further includes a projector 415 for emitting the inspection lights 417a, 417b, 417c and 417d through the respective light emitting elements towards the shell of the container 401, a light receiver 418 having a plurality of light receiving elements 419a, 419b, 419c and 419d disposed in the axial direction of the container 401 at locations opposed to the corresponding light emitting elements 416a, 416b, 416c, and 416d of the projector 415 with the predetermined space therebetween, an arithmetic operation device 420 for calculating the wall thicknesses of the shell portions of the container to be inspected in accordance with the output signals from the light receiver 418, and an elevating device 421 for integrally elevating the light projector 415 and the light receiver 418.

The container 401 conveyed to the second inspecting station by the rotation of the rotary disc 403 is rotated by the motor 448b through the roller 441 and, in the second inspecting station, non-destructive and non-contact type thickness inspections are performed in a short time at many portions of the container 401 in both the axial and circumferential directions by inserting the light receiver 418 into the container 401 through the opening thereof.

The container receiving end portion 409 is located at the upstream end of the second container conveyer 411 for conveying the container 401 which is judged to be a good product in the first and second inspecting stations 407 and 408. The container receiving end portion 409 is positioned at a portion apart from the second inspecting station 408 by the angles of 60° in the rotating direction of the rotary disc 403 as shown in FIGS. 17 and 18.

Only the containers 401 which are conveyed to the container receiving end portion 409 by the rotation of the rotary disc 403 and judged to be good products through the inspections of the first and second inspection stations 407 and 408 are released from the container holders 404 and then transferred to the second container conveyer 411.

The first container discharging station 410 is positioned apart from the second container conveyer 411 by an angle of 60° in the rotating direction of the rotary disc 403. The containers 401 which are determined to be faulty products through the inspection of at least one of the first and second inspecting station 407 and 408 are released from the holders 404 and then discharged externally from the inspecting system through the first container discharging station.

As described hereinbefore, the container feeding station 405, the first inspecting station 407, the second inspecting station 408, the container receiving end portion 409, and the first container discharging station 410 are all arranged around the circumference of the rotary disc 403 apart from each other in this order by the angles of 60° in the direction of rotation thereof, so that the holding, inspecting, releasing and discharging of the containers 401 can be effectively performed through the intermittent rotation of the rotary disc through angles of 60°, respectively.

The container holder 404f, in FIG. 18, is positioned at the intermediate portion between the container feeding station 405 and the container discharging station 410 for the next container holding operation at the container feeding station 405.

The second container conveyer 411 is adapted to convey the container 401 fed from the first container conveyer 402 and received by the container receiving end portions 409 and the conveyer 411 may be constructed by a conveyer belt means, for example, of known type. The third container inspecting station 412 is arranged along the conveying passage of the second container conveyer 411 as shown in FIG. 17.

The third inspecting station 412 performs the inspection of the air tightness of the container 401 two by two each inspecting time, usually, by a known inspecting means.

The containers 401 judged to be faulty products by the third inspecting station 412 are discharged externally through the second discharging station 413.

Accordingly, only the containers 401 which are determined to be good products through the inspections of the first, second and third inspecting stations 407, 408 and 412 are conveyed to the next processing station.

3-2 Effects

According to the inspecting system for the containers made of synthetic resin, the following effects will be attained:

In the automatic and continuous container manufacturing line, the wall thickness inspecting process regarding the heat resisting property of the container is incorporated in the other inspecting processes, for example, for inspecting the existence of the heat resistant resin at the opening portion of the container, whereby the inspection of the container regarding the heat resisting property of the container can be extremely effectively performed and the manufacturing efficiency of the containers having stable qualities can be improved.

What is claimed is:

1. An apparatus for inspecting a wall thickness of a container made of synthetic resin, comprising:

light projector means for projecting an inspection light for insertion into a container made of a synthetic resin so the an open end of said light projector means projects said inspection light toward a wall of the container, light receiver means arranged outside of the container so as to oppose the open end of the light projector means for receiving the inspection light passing through the wall of the container and converting the received light into an electrical signal, inspection position changing means for changing a container inspecting position, and calculation means for calculating the wall thickness of the container on the basis of the electric signal from the light receiver means, wherein the light receiver means comprises a photoelectric transfer element having cooling means incorporated therein for cooling said photoelectric transfer element;

wherein the inspecting position changing means is a rotary means for rotating the container axially and comprises a pair of clamp arms each having a roller follower and a drive roller disposed between said pair of clamp arms; and wherein said calculation means comprises:
   central control means for providing central control of the apparatus,
   interface control means for controlling interfacing of data with the light receiver means,
   drive means for driving a chopper,
   signal processing means for processing signals of the light receiver means and the chopper,
   rotary encoder means for encoding a rotary position of the container, and
   arithmetic operation means for performing arithmetic operations on said data.

2. An apparatus for inspecting a wall thickness of a container made of synthetic resin according to claim 1, wherein the inspecting position changing means is movable in the axial direction of the container while maintaining a constant corresponding relationship between the light projector means and the light receiver means.

3. An apparatus for inspecting a wall thickness of a container made of synthetic resin according to claim 1, wherein the inspection light is an infrared ray having a wavelength of 2 to 5 $\mu$m.

4. An apparatus for inspecting a wall thickness of a container made of synthetic resin according to claim 1, wherein the light projector means is independently movable in a vertical direction.

5. An apparatus for inspecting a wall thickness of a container made of synthetic resin, comprising:

light projector means for projecting an inspection light for insertion into a container made of a synthetic resin so that an open end of said light projector means projects said inspection light toward a wall of the container;

light receiver means arranged outside of the container so as to oppose the open end of the light projector means for receiving the inspection light passing through the wall of the container and converting the received light into an electrical signal;

inspection position changing means for changing a container inspecting position; and calculation means for calculating the wall thickness of the container on the basis of the electric signal from the light receiver means;

means the light receiver means comprises a photoelectric transfer element having cooling means incorporated therein for cooling said photoelectric transfer element; and wherein the inspecting position changing means is a rotary means for rotating the container axially and comprises a pair of clamp arms each having a roller follower and a drive roller disposed between said pair of clamp arms.

* * * * *